United States Patent [19]
Vogt et al.

[11] Patent Number: 6,113,717
[45] Date of Patent: Sep. 5, 2000

[54] METHOD OF MAKING REFASTENABLE, PANT-LIKE DISPOSABLE ABSORBENT ARTICLES

[75] Inventors: Robert Eugene Vogt; Timothy James Blenke, both of Neenah, Wis.

[73] Assignee: Kimberly-Clark Worldwide, Inc., Neenah, Wis.

[21] Appl. No.: 09/215,491

[22] Filed: Dec. 18, 1998

[51] Int. Cl.[7] .................................................. B32B 31/00
[52] U.S. Cl. .......................... 156/73.1; 156/227; 156/264; 156/269
[58] Field of Search ................................... 156/73.1, 196, 156/226, 227, 250, 256, 264, 269; 264/442, 443, 444

[56] References Cited

U.S. PATENT DOCUMENTS

| | | | |
|---|---|---|---|
| H1558 | 7/1996 | Goulait et al. | 156/210 |
| H1674 | 8/1997 | Ames et al. | 604/389 |

(List continued on next page.)

FOREIGN PATENT DOCUMENTS

| | | | |
|---|---|---|---|
| 667899 | 4/1996 | Australia | A61F 13/56 |
| 2096672 | 11/1993 | Canada . | |
| 2103992 A1 | 2/1994 | Canada | A61F 13/64 |
| 2187021 A1 | 10/1995 | Canada | A61F 13/56 |
| 2187366 A1 | 10/1995 | Canada | A61F 13/56 |
| 0 206 208 B1 | 12/1986 | European Pat. Off. | A61F 13/15 |
| 0 217 032 A2 | 4/1987 | European Pat. Off. | D04H 13/00 |
| 0 251 251 A3 | 1/1988 | European Pat. Off. . | |
| 0 463 276 A1 | 1/1992 | European Pat. Off. | A61F 13/62 |
| 0 532 034 A2 | 3/1993 | European Pat. Off. | A61F 13/15 |
| 0 544 703 B1 | 6/1993 | European Pat. Off. | A61F 13/56 |
| 0 696 911 B1 | 2/1996 | European Pat. Off. | A61F 13/66 |
| 0 753 292 A2 | 1/1997 | European Pat. Off. | A61F 13/15 |
| 0 487 758 B1 | 3/1997 | European Pat. Off. . | |
| 0 809 992 A1 | 12/1997 | European Pat. Off. | A61F 13/62 |
| 0 878 180 A2 | 11/1998 | European Pat. Off. | A61F 13/15 |
| 6-77718 U | 11/1994 | Japan | A61F 13/15 |
| 7-213553 | 8/1995 | Japan . | |
| 7-227407 | 8/1995 | Japan . | |
| 7-255773 | 10/1995 | Japan . | |
| 7-299094 | 11/1995 | Japan . | |
| 8-229072 | 9/1996 | Japan | A61F 13/56 |
| 9-287 U | 5/1997 | Japan . | |

(List continued on next page.)

OTHER PUBLICATIONS

Derwent World Patent Database abstract of FR 2762507 A1: Description of RAHALA, "Baby's Disposable Nappy."

Derwent World Patent Database abstract of JP 6–063076 A: Description of Kao Corp. (Kaos), "Throw Away Diaper Or Nappy."

Derwent World Patent Database abstract of JP 95–044941 B2: Description of ZUIKO KK (ZUIK–N), "Simple Solid Diaper For Eliminating Waste of Material by Using Square Shape."

Derwent World Patent Database abstract of JP 9–276334 A: Description of Kao Corp. (Kaos), "Disposable Baby Nappy."

Derwent World Patent Database abstract of JP 11–070143 A: Description of TOYO EISAI KK (TOEI–N), "Disposable Diaper For Adults And Children."

Derwent World Patent Database abstract of JP 11–076299 A: Description of UNI–CHARM KK (UNIC–N), "Disposable Diaper."

*Primary Examiner*—James Sells
*Attorney, Agent, or Firm*—Jeffrey B. Curtin

[57] ABSTRACT

A method of making a refastenable, pant-like, disposable absorbent article includes attaching a pair of opposed side panels to the side edges of an absorbent chassis such hat they extend laterally outward from and between the front and back waist regions of the article. One of the side margins of each side panel is permanently attached to the side edge of the absorbent chassis in one of the waist regions and the other side margin of each side panel is refastenably attached to the side edge of the absorbent chassis in the opposite waist region. The side panels are refastenably attached before the article is packaged to provide the pant-like disposable absorbent article.

27 Claims, 4 Drawing Sheets

OTHER PUBLICATIONS

| | | | |
|---|---|---|---|
| D. 290,780 | 7/1987 | Wistrand | D2/10 |
| D. 389,320 | 1/1998 | Vinnage et al. | D5/63 |
| 1,079,479 | 11/1913 | Earnshaw | 604/392 |
| 1,485,001 | 2/1924 | Wills | 604/392 |
| 1,657,909 | 1/1928 | Abramovich | 604/392 |
| 1,705,194 | 3/1929 | Marinsky | 604/400 |
| 1,762,468 | 6/1930 | Brewer | 604/397 |
| 1,963,334 | 6/1934 | Neilson | 2/237 |
| 2,201,255 | 5/1940 | Wilson, Jr. | 128/284 |
| 2,242,977 | 5/1941 | Marcos | 128/284 |
| 2,475,175 | 7/1949 | Cadous | 2/237 |
| 2,477,914 | 8/1949 | Webb | 128/284 |
| 2,545,761 | 3/1951 | Brink | 128/287 |
| 2,570,963 | 10/1951 | Mesmer | 128/284 |
| 2,630,120 | 3/1953 | Nielson | 128/287 |
| 2,743,725 | 5/1956 | Matthews | 128/284 |
| 2,801,632 | 8/1957 | Burner et al. | 128/284 |
| 2,808,831 | 10/1957 | Winslett | 128/284 |
| 2,830,589 | 4/1958 | Doner | 128/284 |
| 2,833,282 | 5/1958 | Moore | 128/284 |
| 2,910,982 | 11/1959 | Woodward | 128/284 |
| 2,931,361 | 4/1960 | Sostrin | 128/284 |
| 3,039,466 | 6/1962 | Wilson | 128/287 |
| 3,077,193 | 2/1963 | Mann | 128/284 |
| 3,610,244 | 10/1971 | Jones, Sr. | 128/287 |
| 3,638,651 | 2/1972 | Torr | 128/284 |
| 3,653,381 | 4/1972 | Warnken | 128/284 |
| 3,825,006 | 7/1974 | Ralph | 128/287 |
| 3,882,871 | 5/1975 | Taniguchi | 128/287 |
| 4,024,867 | 5/1977 | Mesek | 128/287 |
| 4,051,853 | 10/1977 | Egan, Jr. | 128/287 |
| 4,051,854 | 10/1977 | Aaron | 128/284 |
| 4,066,081 | 1/1978 | Schaar | 128/287 |
| 4,074,716 | 2/1978 | Schaar | 128/287 |
| 4,089,068 | 5/1978 | Swallow | 2/76 |
| 4,090,516 | 5/1978 | Schaar | 128/287 |
| 4,205,679 | 6/1980 | Repke et al. | 128/287 |
| 4,210,143 | 7/1980 | De Jonckheere | 128/287 |
| 4,337,771 | 7/1982 | Pieniak et al. | 128/287 |
| 4,410,327 | 10/1983 | Baggaley | 604/391 |
| 4,500,316 | 2/1985 | Damico | 604/389 |
| 4,515,595 | 5/1985 | Kievit et al. | 604/385 A |
| 4,522,853 | 6/1985 | Szonn et al. | 428/40 |
| 4,525,407 | 6/1985 | Ness | 428/138 |
| 4,563,185 | 1/1986 | Reiter | 604/385 A |
| 4,568,341 | 2/1986 | Mitchell et al. | 604/368 |
| 4,581,772 | 4/1986 | Smith | 2/111 |
| 4,596,055 | 6/1986 | Aach et al. | 2/237 |
| 4,598,528 | 7/1986 | McFarland et al. | 53/430 |
| 4,604,096 | 8/1986 | Dean et al. | 604/385 A |
| 4,610,680 | 9/1986 | LaFleur | 604/385 A |
| 4,610,681 | 9/1986 | Strohbeen et al. | 604/396 |
| 4,615,695 | 10/1986 | Cooper | 604/385 A |
| 4,617,022 | 10/1986 | Pigneul et al. | 604/391 |
| 4,619,649 | 10/1986 | Roberts | 604/396 |
| 4,623,339 | 11/1986 | Ciraldo et al. | 604/359 |
| 4,630,320 | 12/1986 | Van Gompel | 2/406 |
| 4,663,220 | 5/1987 | Wisneski et al. | 428/221 |
| 4,675,918 | 6/1987 | O'Brien | 2/402 |
| 4,699,622 | 10/1987 | Toussant et al. | 604/389 |
| 4,704,116 | 11/1987 | Enloe | 604/385 A |
| 4,726,874 | 2/1988 | Van Vliet | 156/495 |
| 4,728,326 | 3/1988 | Gilles | 604/391 |
| 4,743,239 | 5/1988 | Cole | 604/385 R |
| 4,747,846 | 5/1988 | Boland et al. | 604/38 A |
| 4,753,646 | 6/1988 | Enloe | 604/385 R |
| 4,753,650 | 6/1988 | Williams | 604/389 |
| 4,798,603 | 1/1989 | Meyer et al. | 604/378 |
| 4,801,485 | 1/1989 | Sallee et al. | 428/198 |
| 4,808,252 | 2/1989 | Lash | 156/73.1 |
| 4,826,499 | 5/1989 | Ahr | 604/389 |
| 4,850,988 | 7/1989 | Aledo et al. | 604/385.1 |
| 4,850,992 | 7/1989 | Amaral et al. | 604/389 |
| 4,857,067 | 8/1989 | Wood et al. | 604/389 |
| 4,883,481 | 11/1989 | Blanchard | 604/385.1 |
| 4,892,598 | 1/1990 | Stevens et al. | 156/91 |
| 4,904,252 | 2/1990 | Fitzgerald | 604/385.1 |
| 4,909,802 | 3/1990 | Ahr et al. | 604/385.1 |
| 4,911,702 | 3/1990 | O'Leary et al. | 604/389 |
| 4,917,682 | 4/1990 | Lancaster et al. | 604/385.2 |
| 4,936,840 | 6/1990 | Proxmire | 604/385.2 |
| 4,937,887 | 7/1990 | Schreiner | 2/402 |
| 4,938,753 | 7/1990 | Van Gompel et al. | 604/385.2 |
| 4,944,733 | 7/1990 | Casale | 604/385.1 |
| 4,961,736 | 10/1990 | McCloud | 604/385.1 |
| 4,988,346 | 1/1991 | Pfefferkorn | 604/389 |
| 4,998,929 | 3/1991 | Bjorksund et al. | 604/385.2 |
| 5,019,072 | 5/1991 | Polski | 604/389 |
| 5,019,073 | 5/1991 | Roessler et al. | 604/391 |
| 5,040,244 | 8/1991 | Tubbs | 2/237 |
| 5,062,839 | 11/1991 | Anderson | 604/385.1 |
| 5,066,289 | 11/1991 | Polski | 604/389 |
| 5,069,678 | 12/1991 | Yamamoto et al. | 604/385.1 |
| 5,074,854 | 12/1991 | Davis | 604/385.1 |
| 5,087,253 | 2/1992 | Cooper | 604/385.1 |
| 5,106,382 | 4/1992 | Henry | 604/385.2 |
| 5,106,385 | 4/1992 | Allen et al. | 604/391 |
| 5,110,403 | 5/1992 | Ehlert | 156/580.1 |
| 5,112,326 | 5/1992 | Quadrini | 604/391 |
| 5,135,522 | 8/1992 | Fahrenkrug et al. | 604/385.1 |
| 5,140,757 | 8/1992 | Terada | 34/66 |
| 5,163,932 | 11/1992 | Nomura et al. | 604/385.2 |
| 5,170,505 | 12/1992 | Rohrer | 2/69 |
| 5,176,668 | 1/1993 | Bernardin | 604/368 |
| 5,176,670 | 1/1993 | Roessler et al. | 604/391 |
| 5,176,672 | 1/1993 | Bruemmer et al. | 604/385.1 |
| 5,185,011 | 2/1993 | Strasser | 604/385.1 |
| 5,186,779 | 2/1993 | Tubbs | 156/161 |
| 5,187,817 | 2/1993 | Zolner | 2/400 |
| 5,192,606 | 3/1993 | Proxmire et al. | 428/284 |
| 5,226,992 | 7/1993 | Morman | 156/62.4 |
| 5,242,436 | 9/1993 | Weil et al. | 604/385.2 |
| 5,275,590 | 1/1994 | Huffman et al. | 604/385.2 |
| 5,304,162 | 4/1994 | Kuen | 604/391 |
| 5,340,431 | 8/1994 | Terada | 156/359 |
| 5,358,500 | 10/1994 | Lavon et al. | 604/385.2 |
| 5,368,584 | 11/1994 | Clear et al. | 604/385.2 |
| 5,368,585 | 11/1994 | Dokken | 604/393 |
| 5,370,632 | 12/1994 | Beplate | 604/385.1 |
| 5,370,634 | 12/1994 | Ando et al. | 604/385.1 |
| 5,373,587 | 12/1994 | Sexton | 2/237 |
| 5,374,262 | 12/1994 | Keuhn, Jr. et al. | 604/391 |
| 5,383,872 | 1/1995 | Roessler et al. | 604/391 |
| 5,386,595 | 2/1995 | Kuen et al. | 2/400 |
| 5,397,639 | 3/1995 | Tollini | 428/343 |
| 5,399,219 | 3/1995 | Roessler et al. | 156/259 |
| 5,401,275 | 3/1995 | Flug et al. | 604/391 |
| 5,423,789 | 6/1995 | Kuen | 604/386 |
| 5,445,628 | 8/1995 | Gipson et al. | 604/392 |
| 5,451,219 | 9/1995 | Suzuki et al. | 604/385.2 |
| 5,462,541 | 10/1995 | Bruemmer et al. | 604/391 |
| 5,489,282 | 2/1996 | Zehner et al. | 604/385.1 |
| 5,499,978 | 3/1996 | Buell et al. | 604/385.2 |
| 5,500,063 | 3/1996 | Jessup | 156/85 |
| 5,509,915 | 4/1996 | Hanson et al. | 604/378 |
| 5,527,302 | 6/1996 | Endres et al. | 604/385.1 |
| 5,531,731 | 7/1996 | Brusky | 604/390 |
| 5,531,732 | 7/1996 | Wood | 604/391 |
| 5,537,722 | 7/1996 | Niederhofer et al. | 24/304 |
| 5,540,796 | 7/1996 | Fries | 156/164 |
| 5,545,158 | 8/1996 | Jessup | 604/385.2 |
| 5,545,275 | 8/1996 | Herrin et al. | 156/731 |

| | | | |
|---|---|---|---|
| 5,554,146 | 9/1996 | Niederhofer et al. | 604/391 |
| 5,562,650 | 10/1996 | Everett et al. | 604/378 |
| 5,569,232 | 10/1996 | Roe et al. | 604/385.2 |
| 5,569,234 | 10/1996 | Buell et al. | 604/396 |
| 5,571,586 | 11/1996 | Gobran | 428/41.3 |
| 5,575,784 | 11/1996 | Ames-Ooten et al. | 604/385.1 |
| 5,582,606 | 12/1996 | Bruemmer et al. | 604/385.2 |
| 5,591,152 | 1/1997 | Buell et al. | 604/385.2 |
| 5,593,401 | 1/1997 | Sosalla et al. | 604/385.2 |
| 5,601,546 | 2/1997 | Tanji et al. | 604/385.2 |
| 5,607,416 | 3/1997 | Yamamoto et al. | 604/397 |
| 5,611,789 | 3/1997 | Seth | 604/391 |
| 5,618,366 | 4/1997 | Suekane | 156/73.1 |
| 5,624,420 | 4/1997 | Bridges et al. | 604/365 |
| 5,624,424 | 4/1997 | Saisaka et al. | 604/385.2 |
| 5,624,428 | 4/1997 | Sauer | 604/391 |
| 5,624,429 | 4/1997 | Long et al. | 604/391 |
| 5,626,574 | 5/1997 | Sasaki et al. | 604/385.2 |
| 5,628,738 | 5/1997 | Suekane | 604/385.1 |
| 5,629,063 | 5/1997 | Gobran | 428/40.1 |
| 5,634,916 | 6/1997 | Lavon et al. | 604/385.1 |
| 5,656,111 | 8/1997 | Dilnik et al. | 156/66 |
| 5,662,637 | 9/1997 | Kitaoka et al. | 604/385.2 |
| 5,662,638 | 9/1997 | Johnson et al. | 604/386 |
| 5,665,084 | 9/1997 | Richmond | 604/389 |
| 5,669,897 | 9/1997 | Lavon et al. | 604/385.2 |
| 5,685,874 | 11/1997 | Buell et al. | 604/396 |
| 5,690,626 | 11/1997 | Suzuki et al. | 604/385.2 |
| 5,690,627 | 11/1997 | Clear et al. | 604/385.2 |
| 5,693,038 | 12/1997 | Suzuki et al. | 604/385.2 |
| 5,707,364 | 1/1998 | Coates | 604/391 |
| 5,711,832 | 1/1998 | Glaug et al. | 156/73.1 |
| 5,759,317 | 6/1998 | Justmann | 156/66 |
| 5,772,825 | 6/1998 | Schmitz | 156/164 |
| 5,788,685 | 8/1998 | Ronnberg et al. | 604/385.2 |
| 5,788,797 | 8/1998 | Herrin et al. | 156/73.1 |
| 5,827,259 | 10/1998 | Laux et al. | 604/385.2 |
| 5,827,260 | 10/1998 | Suzuki et al. | 604/385.2 |
| 5,830,206 | 11/1998 | Larsson | 604/390 |
| 5,855,574 | 1/1999 | Kling et al. | 604/392 |
| 5,876,531 | 3/1999 | Jacobs et al. | 156/66 |
| 5,897,545 | 4/1999 | Kline et al. | 604/386 |
| 6,022,430 | 2/2000 | Blenke et al. | 156/73.1 |
| 6,022,431 | 2/2000 | Blenke et al. | 156/73.1 |
| 6,022,432 | 2/2000 | Elsberg et al. | 156/73.1 |
| 6,036,805 | 3/2000 | McNichols | 156/227 |
| B1 4,315,508 | 11/1988 | Bolick | 604/392 |
| B1 4,964,860 | 1/1994 | Gipson et al. | 604/391 |

FOREIGN PATENT DOCUMENTS

| | | | |
|---|---|---|---|
| 11-47188 | 2/1999 | Japan . | |
| 1 520 740 | 8/1978 | United Kingdom | A41B 13/02 |
| 2 244 422 | 12/1991 | United Kingdom | A61F 13/15 |
| 2 267 024 | 11/1993 | United Kingdom | A61F 13/66 |
| 2 288 314 | 10/1995 | United Kingdom | A61F 13/15 |
| 2 288 315 | 10/1995 | United Kingdom | A61F 13/15 |
| 2 288 316 | 10/1995 | United Kingdom | A61F 13/56 |
| 2 291 783 | 2/1996 | United Kingdom . | |
| 2 294 867 | 5/1996 | United Kingdom | A41B 13/10 |
| 2 297 473 | 6/1996 | United Kingdom | A41B 13/04 |
| 2 308 290 | 6/1997 | United Kingdom . | |
| WO 83/04163 A1 | 12/1983 | WIPO | A41B 13/02 |
| WO 90/07313 A1 | 7/1990 | WIPO | A61F 13/15 |
| WO 91/04724 A1 | 4/1991 | WIPO | A61F 13/56 |
| WO 91/08725 A1 | 6/1991 | WIPO | A61F 13/15 |
| WO 92/22274 A1 | 12/1992 | WIPO | A61F 13/15 |
| WO 93/09742 A1 | 5/1993 | WIPO | A61F 13/15 |
| WO 94/17768 A1 | 8/1994 | WIPO | A61F 13/58 |
| WO 95/01148 A1 | 1/1995 | WIPO | A61F 13/56 |
| WO 95/02383 A1 | 1/1995 | WIPO | A61F 13/15 |
| WO 95/13772 A1 | 5/1995 | WIPO | A61F 13/15 |
| WO 95/22951 A1 | 8/1995 | WIPO | A61F 13/15 |
| WO 95/27460 A1 | 10/1995 | WIPO . | |
| WO 95/27462 A1 | 10/1995 | WIPO | A61F 13/56 |
| WO 95/29657 A1 | 11/1995 | WIPO | A61F 13/56 |
| WO 96/03101 A1 | 2/1996 | WIPO | A61F 13/62 |
| WO 96/18315 A1 | 6/1996 | WIPO | A41B 1/10 |
| WO 96/32084 A1 | 10/1996 | WIPO | A61F 13/62 |
| WO 97/15260 A1 | 5/1997 | WIPO | A61F 13/15 |
| WO 97/23186 A1 | 7/1997 | WIPO | A61F 13/58 |
| WO 97/25951 A1 | 7/1997 | WIPO | A61F 13/15 |
| WO 97/31605 A1 | 9/1997 | WIPO . | |
| WO 97/32555 A1 | 9/1997 | WIPO . | |
| WO 97/33547 A1 | 9/1997 | WIPO | A61F 13/66 |
| WO 97/46197 A1 | 12/1997 | WIPO | A61F 13/56 |
| WO 97/47265 A1 | 12/1997 | WIPO . | |
| WO 98/03140 A1 | 1/1998 | WIPO | A61F 13/62 |
| WO 98/18421 A1 | 5/1998 | WIPO | A61F 13/15 |
| WO 98/56328 A1 | 12/1998 | WIPO . | |
| WO 99/07319 A1 | 2/1999 | WIPO . | |

METHOD OF MAKING REFASTENABLE, PANT-LIKE DISPOSABLE ABSORBENT ARTICLES

FIELD OF THE INVENTION

The present invention relates to methods of making disposable absorbent articles which are adapted to contain body exudates. More particularly, the present invention relates to methods of making refastenable, pant-like disposable absorbent articles.

BACKGROUND OF THE INVENTION

It is desired that absorbent articles such as diapers, training pants or incontinence garments provide a close, comfortable fit about the wearer and contain body exudates. Moreover, it is desirable that such absorbent articles, after being soiled, can be removed from the wearer in a convenient and clean manner without undesirably soiling the care giver or surrounding area such as the clothes of the wearer. In certain circumstances, it is also desirable that such absorbent articles are capable of being pulled up or down over the hips of the wearer to allow the wearer or caregiver to easily pull the article on and easily remove the article if it has not been soiled. For example, such absorbent articles can assist in the toilet training of children.

Conventional diapers have typically included a front waist portion and a back waist portion which are releasably connected about the hips of the wearer during use by conventional fasteners such as adhesive tape fasteners or hook and loop type fasteners. For example, the conventional fasteners have typically included a pair of fasteners, such as adhesive tape tabs, located on the outermost corners of the diaper in the back waist region of the diaper and a complimentary fastener, such as a taping panel, located on the outer surface In such a configuration, the diaper has been positioned between the legs of the wearer while the wearer is lying down and the adhesive tape tabs have been releasably attached to the taping panel to secure the back waist portion to the front waist portion of the diaper to secure the diaper about the waist of the wearer. Such conventional diapers are easy to fasten about and remove from the wearer after use without undesirably soiling the care giver. However, such conventional diapers are not provided in a prefastened configuration and, thus, are not configured to be pulled up or down over the hips of the wearer when the fasteners are attached.

Several attempts have been made to provide absorbent articles which effectively contain body exudates, are capable of being pulled up or down over the hips of the wearer and provide ease of cleaning and removal after being soiled. For example, some conventional absorbent articles, such as conventional training pants, have included integral side panels which connect the front waist portion to the back waist portion of the absorbent article. The side panels have been made stretchable such that the waist opening of the absorbent article can expand to allow the absorbent article to be pulled up or down over the hips of the wearer if desired. Such side panels have also been designed such that they may be torn to remove the training pant from the wearer after it has been soiled.

However, many of such attempts have not been completely satisfactory. For example, absorbent articles such as training pants have not always been able to achieve a close conforming fit to the wearer while still being able to expand enough to be pulled up and down over the hips of the wearer. Often such training pants fit the waist of the wearer loosely which can undesirably result in leaks. As a result, many of such articles have not contained bodily exudates as effectively as conventional diaper-type articles which can be adjusted to achieve a more conforming fit to the wearer. Moreover, the inspection and removal of soiled absorbent articles which have integral side panels, such as conventional training pants, have not always been completely satisfactory. For example, the side panels have been difficult to tear when attempting to remove the article from the waist of the wearer instead of pulling the article down over the hips of the wearer.

Accordingly, despite the attempts to develop improved absorbent articles, there remains a need for absorbent articles which can provide the benefits of both conventional training pants and conventional diapers. That is, there remains a need for absorbent articles which conform to the wearer to effectively contain bodily exudates, which are capable of being pulled up and down over the hips and buttocks of the wearer without opening, which are readily secured about and removed from the wearer in a convenient and clean manner and which allow easy inspection by the care giver to assist in determining whether the article is soiled. Moreover, there is a need for improved methods of reliably and consistently making such pant-like disposable absorbent articles.

SUMMARY OF THE INVENTION

In response to the difficulties and problems discussed above, a new method of making refastenable, pant-like disposable absorbent articles have been discovered. In one aspect, the present invention concerns a method of making a refastenable, pant-like, disposable absorbent article which defines a front waist region, a back waist region, a crotch region which extends between and connects said waist regions, a longitudinal direction and a lateral direction. The method includes:

a) providing a continuous web of interconnected absorbent chassis wherein each of the absorbent chassis defines an exterior surface, an interior surface opposite the exterior surface, a pair of laterally opposed side edges and a pair of longitudinally opposed waist edges;

b) providing a pair of opposed side panels which define a first side margin and a second side margin opposite said first side margin;

c) permanently attaching the first side margin of the side panels to the side edge of each of the absorbent chassis in one of the front waist region or the back waist region to provide a permanent joint;

d) selectively cutting the continuous web of interconnected absorbent chassis into discrete absorbent articles;

e) folding each of the discrete absorbent articles about a fold line extending in a lateral direction through the crotch region of the article thereby positioning the waist regions in a facing relationship; and f) refastenably attaching the second side margin of the side panels to the side edge of each of the absorbent chassis in the other waist region to provide a refastenable joint thereby providing the refastenable, pant-like disposable absorbent article.

In another aspect, the present invention concerns a method of making a pant-like, refastenable, disposable absorbent article which includes:

a) providing a continuous web of interconnected absorbent chassis wherein each of the absorbent chassis defines an exterior surface, an interior surface opposite the exterior surface, a pair of laterally opposed side edges and a pair of longitudinally opposed waist edges;

b) permanently attaching a pair of laterally opposed back panels to the side edges of each of the absorbent chassis in one of the front waist region or the back waist region of the absorbent article to provide a permanent joint;

c) refastenably attaching a pair of laterally opposed front panels to the side edges of each of the absorbent chassis in the opposite waist region of the absorbent article to provide a refastenable joint;

d) selectively cutting the continuous web of interconnected absorbent chassis into discrete absorbent articles;

e) folding each of the discrete absorbent articles about a fold line extending in a lateral direction through the crotch region of the article thereby positioning the front panels and the back panels in a facing relationship; and f) connecting the front panels and the back panels together along a pair of laterally opposed side seams to define a waist opening and a pair of leg openings and provide the pant-like, refastenable, disposable absorbent article.

In another aspect, the present invention concerns a method of making a pant-like, refastenable, disposable absorbent article which includes:

a) providing a continuous web of interconnected absorbent chassis;

b) intermittently providing a pair of laterally opposed side panels which define a front portion and a back portion;

c) permanently attaching the back portions of the opposed side panels to the side edges of each of the absorbent chassis in one of the front waist region or the back waist region of the absorbent article to provide a permanent joint;

d) refastenably attaching the front portions of the opposed side panels to the side edges of each of the absorbent chassis in the opposite waist region of the absorbent article to provide a refastenable joint;

e) selectively cutting the continuous web of interconnected absorbent chassis into discrete absorbent articles along a cutting line which intersects the side panels between the front portion and the back portion;

f) folding each of the discrete absorbent articles about a fold line extending in a lateral direction through the crotch region of the article thereby positioning the front portions and the back portions of the side panels in a facing relationship; and g) connecting the front portions and the back portions together along a pair of laterally opposed side seams to define a waist opening and a pair of leg openings and provide the pant-like, refastenable, disposable absorbent.

The present invention advantageously provides methods of making refastenable, pant-like disposable absorbent articles in a reliable and efficient manner. In particular, the present invention provides refastenable, pant-like disposable absorbent articles which are capable of being reliably pulled up or down over the hips of the wearer to assist in the toilet training of the wearer similar to conventional training pants. Moreover, similar to conventional diapers, the pant-like disposable absorbent articles of the present invention can advantageously be applied to and removed from the wearer similar to conventional diapers after they have been soiled with relative ease and cleanliness. Further, the pant-like disposable absorbent articles of the present invention allow easy inspection by the care giver to assist in determining whether the article is soiled similar to conventional diapers.

BRIEF DESCRIPTION OF THE DRAWINGS

The present invention will be more fully understood and further advantages will become apparent when reference is made to the following detailed description of the invention and the accompanying drawings wherein like numerals represent like elements. The drawings are merely representative and are not intended to limit the scope of the appended claims.

DETAILED DESCRIPTION OF THE INVENTION

The present invention concerns methods of making refastenable, pant-like disposable absorbent articles which are adapted to be worn adjacent to the body of a wearer to absorb and contain various exudates discharged from the body. The pant-like absorbent articles are configured to closely conform to the body of the wearer to effectively contain body exudates while being capable of being pulled up or down over the hips and buttocks of the wearer. The absorbent articles are also refastenable such that they can be secured to and removed directly from the waist of the wearer and easily inspected to determine if they have been soiled during use. As such, the pant-like, refastenable, disposable absorbent articles made by the methods of the present invention can function in a similar manner to conventional training pants when left in the prefastened, pant-like configuration or they can be unfastened prior to or during use to function in a refastenable manner similar to conventional diapers. As used herein, the term "disposable" refers to articles which are intended to be discarded after a limited use and which are not intended to be laundered or otherwise restored for reuse.

The pant-like disposable absorbent articles made by the methods of the present invention will be described in terms of a disposable, pant-like diaper article which is adapted to be worn by infants about the lower torso. In particular, the pant-like disposable absorbent articles will be described in terms of a pant-like, refastenable, disposable diaper having prefastened side panels. It is understood that the articles and methods of the present invention are equally adaptable for other types of absorbent articles such as adult incontinent products, training pants, feminine hygiene products, other personal care or health care garments, and the like.

Figure 1:
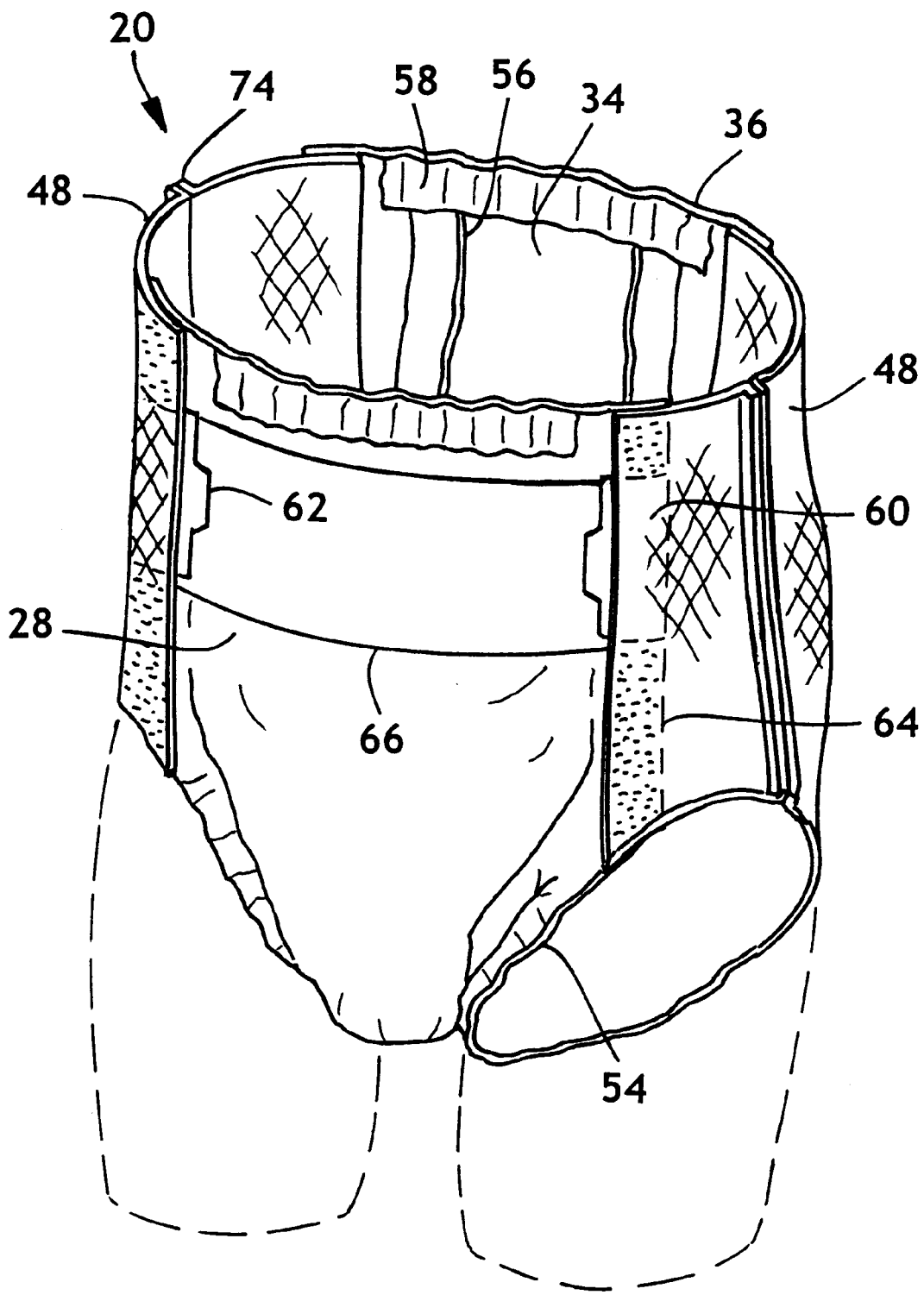
FIG. 1 representatively shows a perspective view of an example of a pant-like, refastenable disposable absorbent article made according to the present invention.
Figure 2:
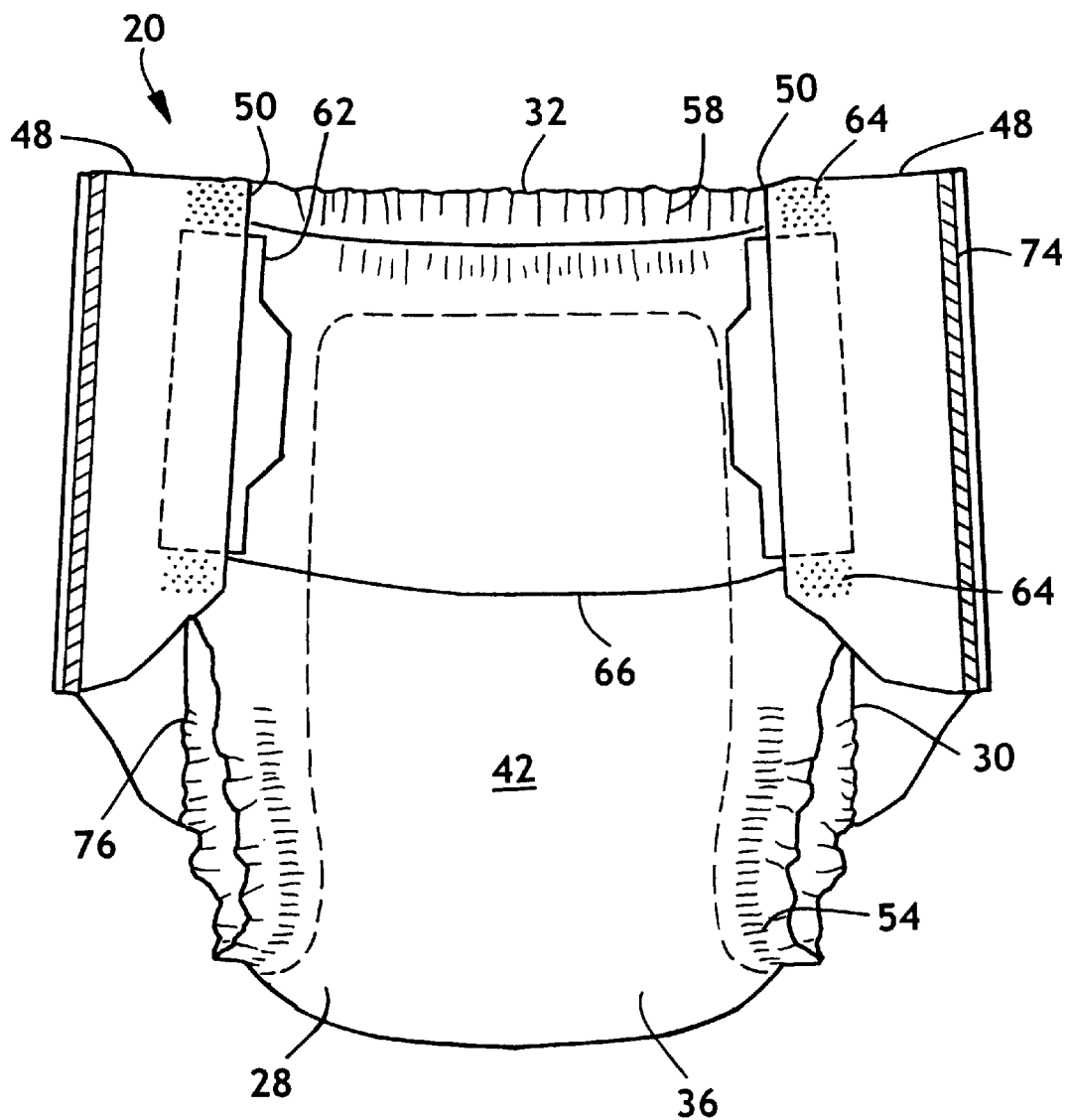
FIG. 2 representatively shows a front plan view of the pant-like, refastenable disposable absorbent article of FIG. 1.
Figure 3:
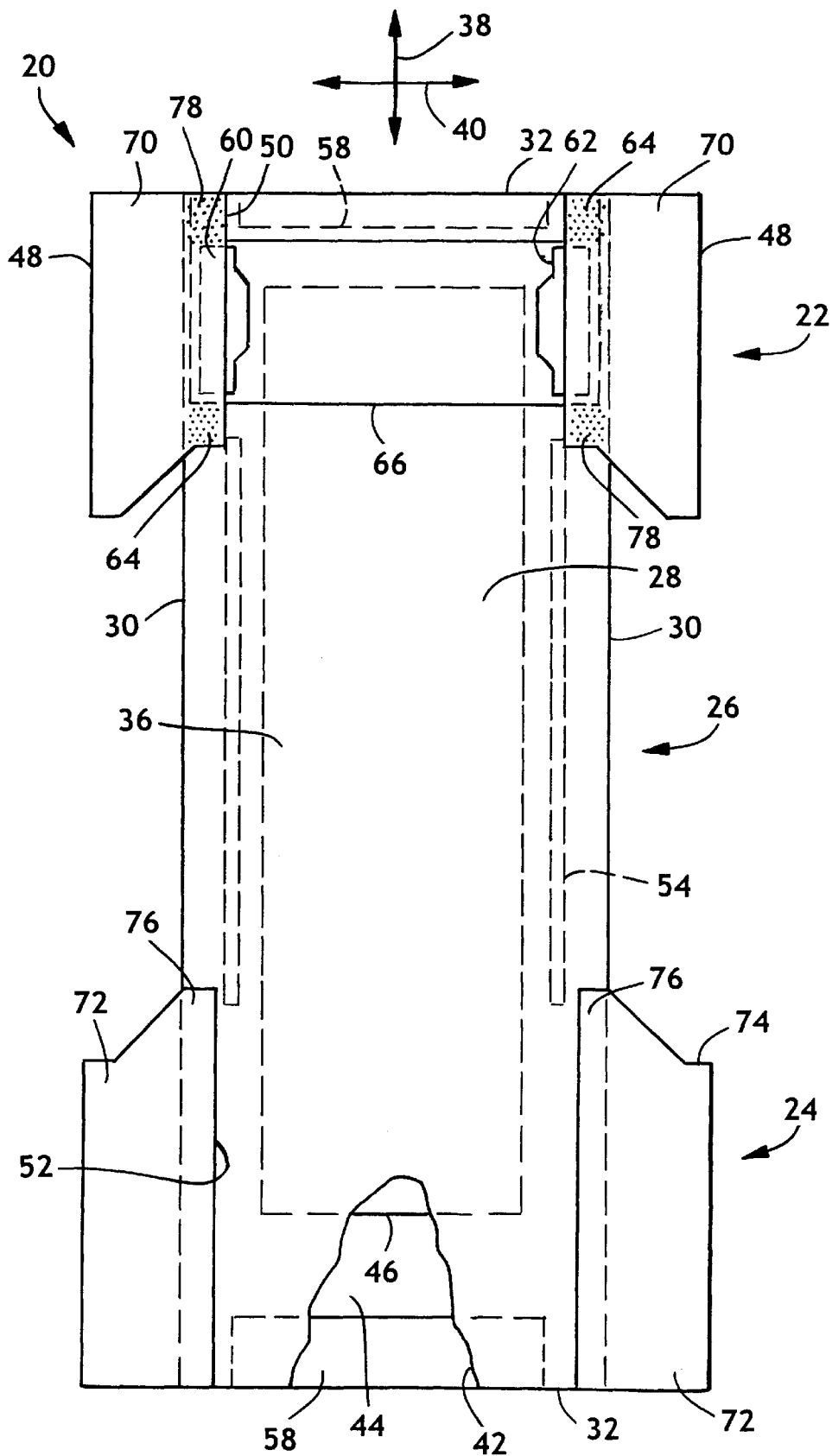
FIG. 3 representatively shows a plan view of the disposable absorbent article of FIG. 1 in an unfastened, stretched and laid flat condition with the surface of the article which contacts the wearer's clothing facing the viewer and with portions of the article partially cut away to show the underlying features.

FIG. 1 representatively illustrates an example of a pant-like, refastenable disposable diaper, as generally indicated at 20, of the present invention. FIG. 2 representatively illustrates a front plan view of the prefastened diaper of FIG. 1. FIG. 3 representatively illustrate the prefastened diaper of FIG. 1 in an unfastened, stretched and laid flat configuration with the surface of the diaper adapted to contact the wearer's clothing facing the viewer and with portions of the diaper partially cut away to show the underlying features. As illustrated in FIG. 3, the diaper 20 defines a front waist region 22, a back waist region 24, a crotch region 26 which extends between and connects the front and back waist regions 22 and 24, a longitudinal direction 38 and a lateral direction 40.

The illustrated diaper 20 includes an absorbent chassis 28 and a pair of laterally opposed side panels 48. The absorbent chassis 28 defines a pair of laterally opposed side edges 30, a pair of longitudinally opposed waist edges 32, an interior surface 34 which is configured to contact the wearer, and an outer surface 36 opposite the interior surface 34 which is configured to contact the wearer's clothing in use. The absorbent chassis 28, as representatively illustrated in FIG. 3, includes an outer cover 42, a bodyside liner 44 which is connected to the outer cover 42 in a superposed relation, and an absorbent core 46 which is located between the outer cover 42 and the bodyside liner 44. The side panels 48 extend laterally outward from and between each opposed side edge 30 of the absorbent chassis 28 of the front and back waist regions 22 and 24.

The front waist region 22 comprises the portion of the diaper 20 which, when worn, is positioned on the front of the wearer while the back waist region 24 comprises the portion of the diaper 20 which, when worn, is positioned on the back of the wearer. The crotch region 26 of the diaper 20 comprises the portion of the diaper 20 which, when worn, is positioned between the legs of the wearer and covers the lower torso of the wearer. The side panels 48 comprise the portions of the diaper which, when worn, are positioned on the side hip regions of the wearer. The laterally opposed side edges 30 of the absorbent chassis 28 and the side panels 48 of the diaper 20 generally define leg openings which may be curvilinear. The waist edges 32 of the absorbent chassis of the diaper 20 and the side panels 48 are configured to encircle the waist of the wearer when worn and provide a waist opening when fastened which defines a waist perimeter dimension.

The illustrated diaper 20 further includes a prefastened, refastenable fastening system 60. The fastening system 60 includes a pair of primary fasteners 62, one located on each of the side panels 48 of the diaper 20, which are releasably engaged with the absorbent chassis 28 adjacent the opposed side edges 30 of the absorbent chassis 28.

The illustrated fastening system 60 further includes releasable bonds 64 adjacent the primary fasteners 62 which assist the primary fasteners in releasably securing the side panels 48 to the absorbent chassis 28. The fastening system 60 may further include an attachment panel 66 located on the outer surface of the absorbent chassis 28 to which the primary fasteners 62 are releasably engaged.

The absorbent chassis 28 is configured to contain and/or absorb any body exudates discharged from the wearer. Whereas, the side panels 48 and the prefastened, refastenable fastening system 60 are configured to maintain the diaper 20 about the waist of the wearer and provide a pant-like appearance. The diaper 20 may further include leg elastics 54, containment flaps 56 and waist elastics 58 as are known to those skilled in the art. It should be recognized that individual components of the diaper 20 may be optional depending upon the intended use of the diaper 20.

The diaper 20 may be of various suitable shapes. For example, in the unfastened configuration as illustrated in FIG. 3, the diaper may have an overall rectangular shape, T-shape or an approximately hour-glass shape. In the shown embodiment, the diaper 20 has a generally I-shape in an unfastened configuration. Examples of diaper configurations suitable for use in connection with the instant application and other diaper components suitable for use on diapers are described in U.S. Pat. No. 4,798,603 issued Jan. 17, 1989, to Meyer et al.; U.S. Pat. No. 5,176,668 issued Jan. 5, 1993, to Bernardin; U.S. Pat. No. 5,176,672 issued Jan. 5, 1993, to Bruemmer et al.; U.S. Pat. No. 5,192,606 issued Mar. 9, 1993, to Proxmire et al., and U.S. Pat. No. 5,509,915 issued Apr. 23, 1996, to Hanson et al., the disclosures of which are herein incorporated by reference. The various aspects and configurations of the invention can provide distinctive combinations of softness, body conformity, reduced red-marking of the wearer's skin, reduced skin hydration, improved containment of body exudates and improved aesthetics.

The various components of the diaper 20 are integrally assembled together employing various types of suitable attachment means, such as adhesive, sonic and thermal bonds or combinations thereof. In the shown embodiment, for example, the outer cover 42 and bodyside liner 44 are assembled to each other and to the absorbent core 46 with adhesive, such as a hot melt, pressure-sensitive adhesive. The adhesive may be applied as a uniform continuous layer of adhesive, a patterned layer of adhesive, a sprayed pattern of adhesive, or an array of separate lines, swirls or dots of adhesive. Similarly, other diaper components, such as the elastic members 54 and 58 and the primary fasteners 62, may be assembled into the diaper 20 article by employing the above-identified attachment mechanisms. Desirably, the majority of the diaper components are assembled together using ultrasonic bonding techniques for reduced manufacturing cost and improved performance.

The outer cover 42 of the absorbent chassis 28 of the diaper 20, as representatively illustrated in FIG. 3, may suitably be composed of a material which is either liquid permeable or liquid impermeable. It is generally preferred that the outer cover 42 be formed from a material which is substantially impermeable to liquids. A typical outer cover can be manufactured from a thin plastic film or other flexible liquid-impermeable material. For example, the outer cover 42 may be formed from a polyethylene film having a thickness of from about 0.013 millimeter (0.5 mil) to about 0.051 millimeter (2.0 mils). If it is desired to present the outer cover 42 with a more clothlike feeling, the outer cover 42 may comprise a polyolefin film having a nonwoven web laminated to the outer surface thereof, such as a spunbond web of polyolefin fibers. For example, a stretch-thinned polypropylene film having a thickness of about 0.015 millimeter (0.6 mil) may have thermally laminated thereto a spunbond web of polypropylene fibers, which fibers have a thickness of about 1.5 to 2.5 denier per filament, which nonwoven web has a basis weight of about 17 grams per square meter (0.5 ounce per square yard). Methods of forming such clothlike outer covers are known to those skilled in the art.

Further, the outer cover 42 may be formed of a woven or nonwoven fibrous web layer which has been totally or partially constructed or treated to impart a desired level of liquid impermeability to selected regions that are adjacent or proximate the absorbent core 46. Still further, the outer cover 42 may optionally be composed of a micro-porous "breathable" material which permits vapors to escape from the absorbent core 46 while still preventing liquid exudates from passing through the outer cover 42. The outer cover 42 can also be embossed or otherwise provided with a matte finish to provide a more aesthetically pleasing appearance.

The bodyside liner 44, as representatively illustrated in FIG. 3, suitably presents a bodyfacing surface which is compliant, soft feeling, and nonirritating to the wearer's skin. Further, the bodyside liner 44 may be less hydrophilic than the absorbent core 46, to present a relatively dry surface to the wearer, and may be sufficiently porous to be liquid permeable, permitting liquid to readily penetrate through its thickness. A suitable bodyside liner 44 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. The bodyside liner 44 is suitably employed to help isolate the wearer's skin from liquids held in the absorbent core 46.

Various woven and nonwoven fabrics can be used for the bodyside liner 44. For example, the bodyside liner may be composed of a meltblown or spunbonded web of polyolefin fibers. The bodyside liner may also be a bonded-carded web composed of natural and/or synthetic fibers. The bodyside liner may be composed of a substantially hydrophobic material, and the hydrophobic material may, optionally, be treated with a surfactant or otherwise processed to impart a desired level of wettability and hydrophilicity. In a particular embodiment of the present invention, the bodyside liner 44 comprises a nonwoven, spunbond, polypropylene fabric composed of about 2.8–3.2 denier fibers formed into a web having a basis weight of about 20 grams per square meter and a density of about 0.13 gram per cubic centimeter. The fabric may be surface treated with about 0.3 weight percent of a surfactant commercially available from Hodgson Textile Chemicals, Inc. under the trade designation AHCOVEL Base N-62. The surfactant may be applied by any conventional means, such as spraying, printing, brush coating or the like. The surfactant may be applied to the entire bodyside liner 44 or may be selectively applied to particular sections of the bodyside liner 44, such as the medial section along the longitudinal centerline of the diaper, to provide greater wettability of such sections. The bodyside liner 44 may further include a lotion or treatment applied thereto to which is configured to treat or be transferred to the wearer's skin.

The absorbent core 46 of the diaper 20, as representatively illustrated in FIG. 3, may suitably comprise a matrix of hydrophilic fibers, such as a web of cellulosic fluff, mixed with particles of a high-absorbency material commonly known as superabsorbent material. In a particular embodiment, the absorbent core 46 comprises a matrix of cellulosic fluff, such as wood pulp fluff, and superabsorbent hydrogel-forming particles. The wood pulp fluff may be exchanged with synthetic, polymeric, meltblown fibers or with a combination of meltblown fibers and natural fibers. The superabsorbent particles may be substantially homogeneously mixed with the hydrophilic fibers or may be non-uniformly mixed. The fluff and superabsorbent particles may also be selectively placed into desired zones of the absorbent core 46 to better contain and absorb body exudates. The concentration of the superabsorbent particles may also vary through the thickness of the absorbent core 46. Alternatively, the absorbent core 46 may comprise a laminate of fibrous webs and superabsorbent material or other suitable means of maintaining a superabsorbent material in a localized area.

The absorbent core 46 may have any of a number of shapes. For example, the absorbent core may be rectangular, I-shaped, or T-shaped. It is generally preferred that the absorbent core 46 be narrow in the crotch area of the diaper 20. It has been found that the absorbent chassis 28 of the present invention is particularly useful when the width dimension in the crotch region 26 is from about 2.5 to about 12.7 centimeters (1.0 to about 5.0 inches), desirably no more than about 7.6 centimeters (3.0 inches) and more desirably no more than about 5.1 centimeters (2.0 inches). The narrow crotch width dimension of the absorbent chassis 28 allows the absorbent chassis 28 to better fit between the legs of the wearer. The size and the absorbent capacity of the absorbent core 46 should be compatible with the size of the intended wearer and the liquid loading imparted by the intended use of the absorbent article.

The high-absorbency material can be selected from natural, synthetic, and modified natural polymers and materials. The high-absorbency materials can be inorganic materials, such as silica gels, or organic compounds, such as crosslinked polymers. The term "crosslinked" refers to any means for effectively rendering normally water-soluble materials substantially water insoluble but swellable. Such means can include, for example, physical entanglement, crystalline domains, covalent bonds, ionic complexes and associations, hydrophilic associations such as hydrogen bonding, and hydrophobic associations or Van der Waals forces.

Examples of synthetic, polymeric, high-absorbency materials include the alkali metal and ammonium salts of poly (acrylic acid) and poly(methacrylic acid), poly (acrylamides), poly(vinyl ethers), maleic anhydride copolymers with vinyl ethers and alpha-olefins, poly(vinyl pyrolidone), poly(vinyl morpholinone), poly(vinyl alcohol), and mixtures and copolymers thereof. Further polymers suitable for use in the absorbent core include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthum gum, locust bean gum, and the like. Mixtures of natural and wholly or partially synthetic absorbent polymers can also be useful in the present invention. Such high-absorbency materials are well known to those skilled in the art and are widely commercially available. Examples of superabsorbent polymers suitable for use in the present invention are SANWET IM 3900 polymer available from Hoechst Celanese located in Portsmouth, Va. and DOW DRYTECH 2035LD polymer available from Dow Chemical Co. located in Midland, Mich.

The high absorbency material may be in any of a wide variety of geometric forms. As a general rule, it is preferred that the high absorbency material be in the form of discrete particles. However, the high absorbency material may also be in the form of fibers, flakes, rods, spheres, needles, or the like. As a general rule, the high absorbency material is present in the absorbent body in an amount of from about 5 to about 90 weight percent based on total weight of the absorbent core 46.

Optionally, a substantially hydrophilic tissue wrapsheet (not illustrated) may be employed to help maintain the integrity of the airlaid fibrous structure of the absorbent core 46. The tissue wrapsheet is typically placed about the absorbent body over at least the two major facing surfaces thereof and composed of an absorbent cellulosic material, such as creped wadding or a high wet-strength tissue. In one aspect of the invention, the tissue wrapsheet can be configured to provide a wicking layer which helps to rapidly distribute liquid over the mass of absorbent fibers comprising the absorbent body. The wrapsheet material on one side of the absorbent fibrous mass may be bonded to the wrapsheet located on the opposite side of the fibrous mass to effectively entrap the absorbent core 46.

As representatively illustrated in FIG. 1, the absorbent chassis 28 of the disposable diaper 20 may include a pair of containment flaps 56 which are configured to provide a barrier to the lateral flow of body exudates. The containment flaps 56 may be located along the laterally opposed side edges 30 of the absorbent chassis 28. Each containment flap 56 typically defines an unattached edge which is configured to maintain an upright, perpendicular configuration in at least the crotch region 26 of the diaper 20 to form a seal against the wearer's body. The containment flaps 56 may extend longitudinally along the entire length of the absorbent chassis 28 or may only extend partially along the length of the absorbent chassis 28. When the containment flaps 56 are shorter in length than the absorbent chassis 28, the containment flaps 56 can be selectively positioned anywhere along the side edges 30 of the absorbent chassis 28. In a particular aspect of the invention, the containment flaps 56 extend along the entire length of the absorbent chassis 28 to better contain the body exudates.

Such containment flaps 56 are generally well known to those skilled in the art. For example, suitable constructions and arrangements for containment flaps 56 are described in U.S. Pat. No. 4,704,116 issued Nov. 3, 1987, to K. Enloe the disclosure of which is hereby incorporated by reference.

The disposable diaper 20 of the different aspects of the present invention may further include elastics at the waist edges 32 and side edges 30 of the absorbent chassis 28 of the diaper 20 to further prevent leakage of body exudates and support the absorbent chassis 28. For example, as representatively illustrated in FIGS. 1–3, the diaper 20 of the present invention may include a pair of leg elastic members 54 which are connected to the laterally opposed side edges 30 of the absorbent chassis 28 in the crotch region 26 of the diaper 20 and a pair of waist elastic members 58 which are connected to the longitudinally opposed waist edges 32 of the absorbent chassis 28 of the diaper 20. The leg elastics 54 and waist elastics 58 are generally adapted to fit about the legs and waist of a wearer in use to maintain a positive, contacting relationship with the wearer to effectively reduce or eliminate the leakage of body exudates from the diaper 20.

Materials suitable for use as the leg elastics 54 and waist elastics 58 are well known to those skilled in the art. Exemplary of such materials are sheets or strands or ribbons of a polymeric, elastomeric material which are adhered to the outer cover 42 in a stretched position, or which are attached to the outer cover 42 while the outer cover is pleated, such that elastic constrictive forces are imparted to the outer cover 42. The leg elastics may also include such materials as polyurethane, synthetic and natural rubber.

As representatively illustrated in FIGS. 1–3, the diaper 20 further includes a pair of laterally opposed side panels 48. Each side panel 48 defines a first side margin 50 which is joined to the side edge 30 of the absorbent chassis 28 in the front waist region 22 and a second side margin 52 which is joined to the side edge 30 of the absorbent chassis 28 in the back waist region 24. The illustrated side panels 48 are permanently connected to the side edges 30 of the absorbent chassis 28 in at least one of the waist regions 22 and 24 and releasably attached to the side edges 30 of the absorbent chassis 28 in the opposite waist region.

For example, as illustrated in FIGS. 1–3, the second side margins 52 of the side panels 48 of the diaper 20 may be permanently secured to and extend laterally beyond the side edges 30 of the diaper 20 in the back waist region 24 of the diaper 20 to provide a permanent joint 76. The side panels 48 are permanently connected to the diaper 20 along permanent joint 76 using attachment means known to those skilled in the art such as adhesive, thermal or ultrasonic bonding. As discussed above, the side panels 48 are desirably permanently connected to the absorbent chassis 28 of the diaper 20 using ultrasonic bonding for improved manufacturing efficiency and reduced raw material cost. In such a configuration, the first side margin 50 of each of the side panels 48 is refastenably attached to the side edges 30 of the absorbent chassis 28 in the front waist region 22 of the diaper 20 to provide a refastenable joint 78 as will be discussed herein in more detail with respect to the description of the fastening system 60. The refastenable joint 78 in such a configuration is located on the front abdominal region of the wearer for easy access to the care giver.

Alternatively, the side margins of the side panels 48 may be permanently connected to the side edges 30 of the absorbent chassis 28 in the front waist region 22 and refastenably attached to the side edges 30 of the absorbent chassis 28 in the back waist region 24 of the diaper if it is desired that the fasteners be located towards the back of the wearer. Such a configuration may be desirable to prevent a wearer from unfastening the article prematurely.

Each of the side panels 48 may include one or more individual, distinct pieces of material. For example, in the illustrated embodiments, each side panel 48 includes a front side panel 70 and a back side panel 72. The front side panel 70 includes the first side margin 50 which is refastenably attached to the side edges 30 of the absorbent chassis 28 in the front waist region 22 of the diaper 20. The back side panel 72 includes the second side margin 52 which is permanently connected to the side edges 30 of the absorbent chassis 28 in the back waist region 24 of the diaper 20. In such a configuration, the laterally outward edge of the front side panel 70 is connected to the laterally outward edge of each back side panel 72 to provide a side seam 74 as illustrated in FIG. 2. Desirably, the laterally outward edges of the front and back side panels 70 and 72 are attached to each other along the side seam 74 using ultrasonic bonding for improved manufacturing efficiency and reduced raw material cost. Side panels 48 having such front and back side panels 70 and 72 provide improved manufacturability. In an alternative configuration, each side panel 48 may include a single piece of material which is folded over upon itself during manufacturing along a fold line located in a similar location to the side seam 74.

Materials suitable for the side panels 48 of the diaper 20 are generally known to those skilled in the art. For example, suitable materials for the side panels 48 include those materials described above as being suitable for the outer cover 42 or bodyside liner 44 of the absorbent chassis 28 of the diaper 20 such as woven and nonwoven materials or laminates of such materials. Desirably, the side panels 48 are elastic or stretchable to provide improved fit about the wearer. For example, the side panels 48 may comprise a stretch-thermal laminate (STL), neck-bonded laminate (NBL), or stretch-bonded laminate (SBL) material. Methods of making such materials are well known to those skilled in the art and described in U.S. Pat. No. 4,663,220 issued May 5, 1987 to Wisneski et al., U.S. Pat. No. 5,226,992 issued Jul. 13, 1993 to Mormon, and European Patent Application No. EP 0 217 032 published on Apr. 8, 1987 in the names of Taylor et al., the disclosures of which are hereby incorporated by reference. When made with elastic materials, the side panels 48 are desirably capable of elongating in the lateral direction 40 from about 10 to about 400 percent, more desirably at least about 100 percent, even more desirably from about 100 to about 300 percent, and still yet more desirably from about 150 to about 250 percent for improved fit and performance. The stretchability of the side panels allows the side panels 48 to stretch over and around the hips of the wearer as the prefastened diaper is pulled on while still maintaining proper fit at the waist after the diaper is correctly positioned on the wearer.

Desirably, the side panels 48 are a neck-bonded laminate material for improved manufacturing due to it's ability to stretch in the cross machine direction. For example, in a particular embodiment, the side panels 48 include a neck-bonded laminate material which includes a urethane film having a basis weight of about 15 grams per square meter and commercially available from Shawmut Mills, a business having offices in West Bridgewater Massachusetts, under the trade designation SHAWMUT TX-1560 sandwiched between two layers of necked, stretched spunbond. Each spunbond layer has a basis weight of about 16 grams per square meter and is composed of 3.0 denier polypropylene fibers. The composite is laminated together with an adhesive spray at an add-on rate of about 0.3 grams per square meter. A suitable adhesive is available from Findley Adhesive under the trade designation FINDLEY 2525A. Such a neck-bonded laminate material is generally capable of elongating in the cross machine direction about 185 percent.

The absorbent article of the different aspects of the present invention further includes a prefastened, refastenable fastening system 60 for securing the absorbent article about the waist of the wearer. The fastening system 60 includes fasteners located on one of the waist regions 22 and 24 of the diaper 20 which are configured to releasably engage the opposite waist region of the diaper 20 to maintain the diaper about the waist of the wearer. The use of fasteners which are refastenable or releasably engageable allows for ease of securing and removing the diaper 20 from the waist of the wearer without undesirably soiling the wearer. The use of refastenable fasteners further readily allows for the inspection of the inside of the diaper 20 to determine if it has been soiled with the ability to refasten if it is not soiled.

As representatively illustrated in FIGS. 1–3, the prefastened, refastenable fastening system 60 of the present invention includes a pair of primary fasteners 62, one located on each of the side panels 48 of the diaper 20, which are refastenably engaged with the absorbent chassis 28 along the opposed side edges 30 of the absorbent chassis 28. The fastening system 60 may also include releasable bonds 64 which assist the primary fasteners 62 in releasably securing the side panels 48 to the absorbent chassis 28. When the primary fasteners 62 are refastenably engaged, the side edges 30 of the absorbent chassis 28 and edges of the side panels 48 define leg openings which are configured to encircle the legs of the wearer and the waist edges 32 of the absorbent chassis 28 and the edges of the side panels 48 opposite those defining the leg openings define a waist opening which is configured to encircle the waist of the wearer.

In the illustrated embodiments, the primary fasteners 62 are adhered to the first side margins 50 of the side panels 48 and are refastenably engaged with the exterior surface 36 of the absorbent chassis 28 along the side edges 30 of the absorbent chassis 28 in the front waist region 22 of the diaper 20. The location of the primary fasteners 62 along the side margins 50 of the side panels 48 as opposed to being located along the side seam 74 between the front and back panels 70 and 72 provides the caregiver improved access to the primary fasteners 62 as the fasteners will be located towards the front of the wearer. Desirably, the outboard edges of the primary fasteners 62 are located inward from the side seam 74 or the laterally outboard edge of the article a distance of at least about 1.9 centimeters and more desirably at least about 3.8 centimeters to provide such improved access.

In such a configuration, the side panels 48 are permanently connected to the side edges 30 of the absorbent chassis 28 in the back waist region 24 of the diaper 20 and refastenably attached to the side edges 30 of the absorbent chassis 28 in the front waist region 22 via the primary fasteners 62. Alternatively, as discussed above, the side panels 48 may be permanently connected to the side edges 30 of the absorbent chassis 28 in the front waist region 22 and the primary fasteners 62 on the side panels 48 may be refastenably engaged to the exterior surface 36 of the absorbent chassis 28 to the side edges 30 of the absorbent chassis 28 in the back waist region 24 of the diaper 20. The primary fasteners 62 may be adhered to the side panels 48 by any means known to those skilled in the art such as adhesive bonds, sonic bonds or thermal bonds.

Desirably, the primary fasteners 62 are refastenably engaged directly with the outer surface of the outer cover 42 of the absorbent chassis 28 of the diaper 20 to provide improved fit and ease of fastening. Alternatively, as representatively illustrated in FIG. 3, the disposable diaper 20 of the present invention may further include an attachment panel 66 located on the outer cover 42 in one of the waist regions 22 and 24 of the diaper 20. In such a configuration, the primary fasteners 62 are refastenably engaged with the attachment panel 66 to maintain the diaper 20 about the waist of the wearer. The attachment panel 66 may include two separate panels located along the opposed side edges of the absorbent chassis 28 in one of the waist regions 22 and 24 of the diaper 20. Alternatively, the attachment panel 66 may include a single piece of material which extends substantially across the respective waist region of the diaper 20.

In the different aspects of the present invention, the primary fasteners 62 are refastenably engaged with the outer surface of the opposite waist region 22 and 24 of the diaper 20 before the diaper 20 is placed on the wearer to provide a prefastened, refastenable, pant-like disposable diaper. In such a configuration, the pant-like, refastenable diaper 20 can be pulled on or off over the legs and hips of the wearer. If the pant-like diaper 20 becomes soiled during use, the primary fasteners 62 can be disengaged to easily remove the diaper 20 from the waist of the wearer with reduced risk of undesirably soiling the clothes or legs of the wearer. The primary fasteners 62 can also be easily disengaged to inspect the diaper 20 for possible soiling or to first apply the product to the wearer if desired. Thus, the diaper 20 is configured to be pulled on or off over the hips of the wearer such as conventional training pants and can be readily applied or removed by disengaging the fasteners similar to conventional diaper articles. Moreover, the primary fasteners 62 can be repositioned if necessary after the prefastened diaper 20 has been pulled on over the legs and hips of the wearer to adjust the fit of the diaper to the wearer.

Suitable fasteners are well known to those skilled in the art and can include adhesive tape tab fasteners, hook and loop fasteners, mushroom fasteners, snaps, pins, belts and the like, and combinations thereof. For example, as representatively illustrated in FIG. 3, the primary fasteners 62 may be hook type fasteners and the outer cover 42 or attachment panel 66 may be configured to function as a complimentary loop type fastener. Desirably, the primary fasteners 62 are hook type fasteners which are refastenably engageable directly with the outer cover 42. Such an arrangement provides the ability to vary the size of the waist opening in very small increments over a wide range to fit the waist of the wearer.

The pant-like, refastenable disposable absorbent article of the present invention may further include releasable bonds 64 for improved reliability of maintaining the article in the prefastened condition particularly when it is being pulled on or off over the hips of the wearer. Absorbent articles including such releasable bonds and methods of making such are further described in U.S. Patent Application entitled "DISPOSABLE ABSORBENT ARTICLES HAVING PASSIVE SIDE BONDS AND ADJUSTABLE FASTENING SYSTEMS" filed in the name of Elsberg on Jun. 19, 1998 and assigned U.S. Ser. No. 09/100,574, and U.S. Patent Application entitled "METHOD OF MAKING AN ABSORBNET ARTICLE WITH PREFASTENED SIDE PANELS AND ABSORBENT ARTICLES MADE BY THE SAME" filed in the name of McNichols on Jun. 19, 1998 and assigned U.S. Ser. No. 09/100,825, the disclosures of which are hereby incorporated by reference.

For example, as representatively illustrated in FIGS. 1–3, the pant-like diaper 20 may include a pair of releasable bonds 64 which releasably connect the side panels 48 to the front waist region 22 of the diaper 20. In such a configuration, the releasable bonds 64 assist the fastening system 60 and, in particular, the primary fasteners 62 in maintaining the diaper 20 in a prefastened condition as the diaper 20 is pulled up or down over the hips of the wearer. Moreover, the releasable bonds 64 assist the primary fasteners 62 in preventing movement and shifting of the waist regions 22 and 24 and side panels 48 relative to each other for improved fit and performance. The releasable bonds 64 also provide improved hip coverage and prevent rollover or folding of the side edges 30 and waist edges 32 of the absorbent chassis 28 of the prefastened diaper 20 as it is pulled over the wearers hips. Such prevention of rollovers and foldovers can reduce the level of contact between the fasteners and the skin of the wearer which can desirably result in reduced skin irritation and redness.

As shown in FIG. 3, the releasable bonds 64 may be located longitudinally adjacent to the primary fasteners 62 on the first side margins 50 of the side panels 48 in the front waist region 22 of the diaper 20. In such a configuration, the releasable bonds 64 connect the side margins 50 of the side panels 48 to the side edges 30 of the absorbent chassis 28 of the diaper 20. The releasable side bonds 64 may be located on the side margins 50 in any manner which provides the desired improved fastening.

In the illustrated embodiments, the releasable bonds 64 connect the respective side panel 48 and side edge 30 of the absorbent chassis 28 in the front waist region 22 in a facing relationship. The releasable bonds 64 can be provided by any type of bonding such as thermal, adhesive and ultrasonic bonding as are well known to those skilled in the art and may be discrete point bonds, dashed lines, continuous lines, discontinuous lines and the like or combinations thereof. Moreover, the releasable bonds 64 may have any shape such as circular, square, triangular and the like. Desirably, the releasable bonds 64 are ultrasonic point bonds for improved manufacturing efficiency. In such a configuration, the ultrasonic releasable bonds 64 will be destroyed upon the first opening of the pant-like diaper 20.

In certain aspects of the invention, the location of the releasable bonds 64 and the respective primary fasteners 62 can be selectively varied to tailor the fit of the diaper 20 for different sized wearers. For example, the location of the primary fasteners 62 and releasable bonds 64 may be varied during the manufacturing process such that the same process can produce prefastened, refastenable, pant-like diapers suitable for a range of sizes which can encompass several conventional sized diapers.

The releasable bonds 64 are configured to assist the primary fasteners 62 in maintaining the diaper 20 in a prefastened configuration as the diaper 20 is pulled on and off over the hips of the wearer and during use. Thus, it is desirable that the releasable bonds 64 provide adequate shear strength for assisting the primary fasteners 62. For example, in a particular embodiment, the releasable bonds 64 define a shear strength of at least about 50 grams and desirably at least about 100 grams. For example, the releasable bonds 64 may define a shear strength of from about 100 to about 4000 grams and desirably from about 500 to about 2000 grams. As used herein, the term "shear strength" refers to the value obtained when subjecting the side bonds to the Shear Strength Test described herein. Shear strength values less than those described above may not prevent the separation of the respective waist region 22 and 24 and side panel 48 from each other during the application and use of the diaper 20.

The releasable bonds 64 are also configured to be readily broken such that the caregiver can easily pealingly disengage the side panels to remove the diaper 20 from the wearer after it has been soiled, to inspect the diaper for soiling or to initially position the diaper 20 on the wearer if desired. Thus, it is desirable that the releasable bonds 64 define a relatively low peel strength such that the caregiver can readily disengage the primary fasteners 62 and break the releasable bonds 64 to separate the waist region 22 or 24 from the side panels 48 to remove the diaper 20 from the waist of the wearer similar to conventional diapers which are not prefastened. For example, in a particular embodiment, the releasable bonds 64 define a peel strength of no more than about 1500, desirably no more than about 1000 grams and more desirably no more than about 800 grams. As used herein, the term "peel strength" refers to the value obtained when subjecting the side bonds to the Peel Strength Test described herein. Peel strength values greater than those described above may not be readily breakable and may undesirably result in tearing of other portions of the diaper 20.

The different aspects of the present invention advantageously provide pant-like, refastenable disposable absorbent articles which can include the combination of releasable bonds and refastenable fasteners. The fasteners are prefastened to refastenably engage the side panels 48 with the front and back waist portions to allow the absorbent article to be pulled up or down over the hips of the wearer such as conventional training pants. Moreover, the fastening system can be used to refastenably engage and adjust the front and back waist portions of the absorbent article to maintain the absorbent article about the waist of the wearer after the article has been pulled on in a similar manner to conventional diapers. The releasable bonds assist the fastening system in maintaining the article in a prefastened condition as the article is pulled up or down over the hips of the wearer. Moreover, the fastening system prevent movement and shifting of the waist portions relative to each other for improved manufacturability, fit and performance. The fastening system also prevent the rollover or folding in of the side and waist edges of the prefastened absorbent article as it is pulled over the wearers hips.

As a result, the absorbent articles of the present invention are designed to conform to the body of the wearer to effectively contain bodily exudates while still being capable of being reliably pulled up or down over the hips of the wearer to assist in the toilet training of the wearer. Moreover, similar to conventional diapers, the absorbent articles of the present invention can advantageously be applied to and removed from the wearer with relative ease and cleanliness.

The methods of the different aspects of the present invention are directed at reliably and consistently providing the pant-like, refastenable disposable absorbent articles described herein such as that representatively illustrated in FIGS. 1–3. For example, as representatively illustrated in FIG. 4, the methods can include providing a continuous web of interconnected absorbent chassis 80 moving in the direction indicated by the arrow associated therewith. In such a configuration, the front waist region of the leading chassis may be connected to the back waist region of the trailing chassis to form the continuous web of interconnected absorbent chassis 80. Alternatively, the back waist region of the leading chassis may be connected to the front waist region of the trailing chassis or the chassis may be arranged in a front-to-front/back-to-back relationship.

The continuous web of interconnected absorbent chassis 80 may be provided by means known to those skilled in the art. For example, a web of interconnected absorbent chassis 80, such as the absorbent chassis 28 illustrated in FIG. 3, may be provided by intermittently placing individual absorbent cores 46 between a continuously moving web of outer cover material and a continuously moving web of bodyside liner material at spaced apart locations. Additional components, such as the leg elastics 54, containment flaps 56 and waist elastics 58, may also be connected to the continuously moving web of interconnected absorbent chassis 80. The different components of the diaper 20 may be connected together by means known to those skilled in the art such as, for example, adhesive, thermal or ultrasonic bonding. Desirably, most of the components are connected using ultrasonic bonding for improved manufacturing efficiency and reduced raw material cost.

Figure 4:
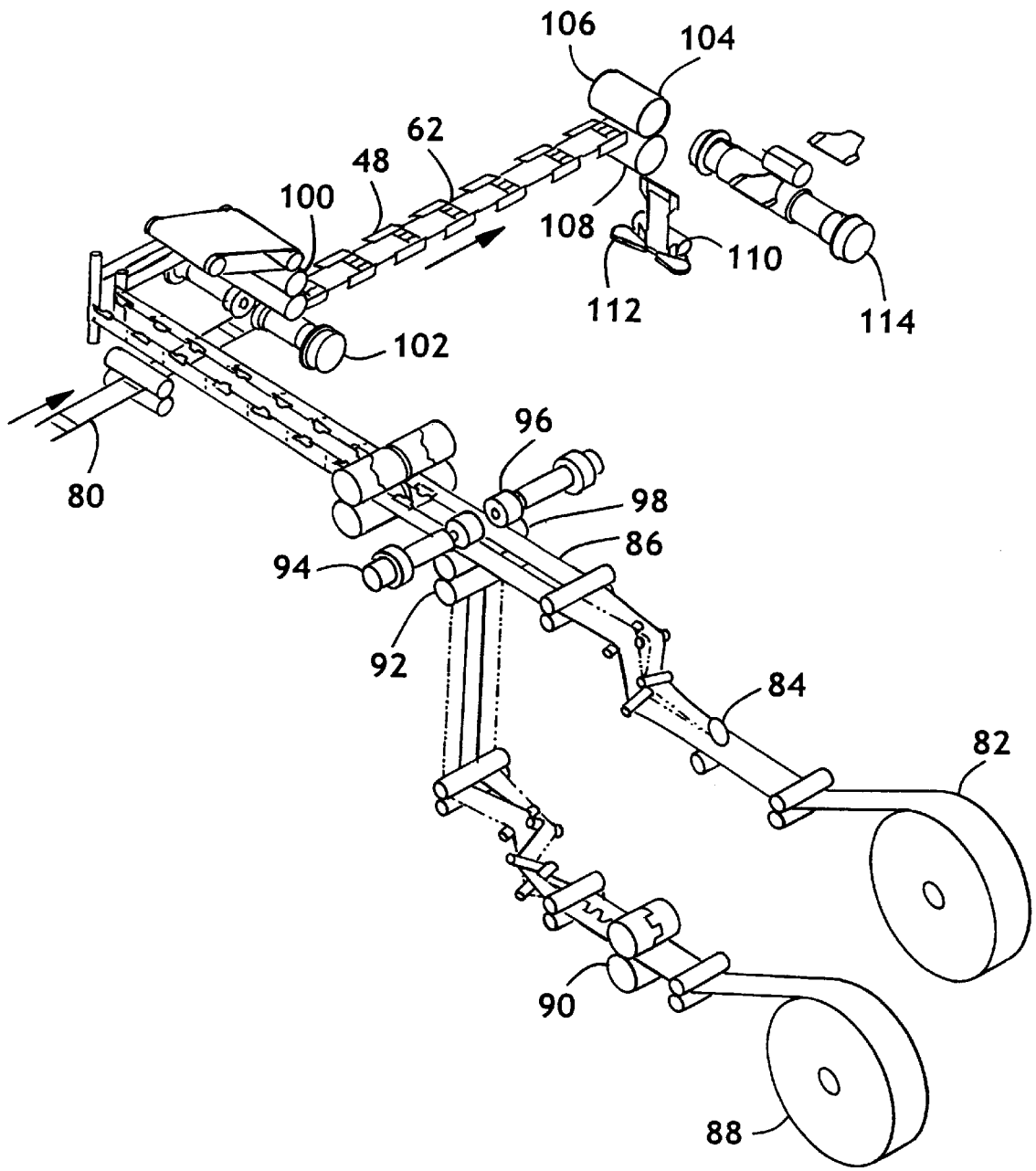
FIG. 4 representatively shows a schematic view of an example of a method of making refastenable, pant-like disposable absorbent articles according to the present invention.

As illustrated in FIG. 4, a pair of laterally opposed side panels 48 having primary fasteners 62 attached thereto are also attached to the side edges of the continuously moving web of interconnected absorbent chassis 80. In such a configuration, the primary fasteners 62 may be refastenably engaged with the outer surface of the absorbent chassis 28 of each diaper. For example, as representatively illustrated in FIGS. 1 and 2, the primary fasteners 62 located on the side margins 50 of each of the side panels 48 may be refastenably engaged with the outer surface 36 of the absorbent chassis 28 of the diaper 20 in the front waist region 22 of the diaper 20. Alternatively, the primary fasteners 62 located on the side margins 50 of each of the side panels 48 may be refastenably engaged with the outer surface 36 of the absorbent chassis 28 of the diaper 20 in the back waist region 24. As discussed above, each diaper 20 may include an attachment panel 66 located on the outer cover 42 to which the primary fasteners 62 are refastenably engaged. Alternatively, the primary fasteners 62 may refastenably engage the outer cover 42 of the absorbent chassis 28 of the diaper 20 directly without requiring a separate fastening panel.

The laterally opposed side panels 48 may be supplied by means known to those skilled in the art. For example, as illustrated in FIG. 4, a roll of side panel material 82 may be unwound and cut by slitter 84 to provide two webs of spaced apart, interconnected side panels 86. As illustrated, the primary fasteners 62 can be provided by unwinding a roll of fastener material 88, passing the web of fastener material through a die cutter 90 which selectively cuts the web of fastener material into two webs of spaced apart, fastener material. The individual primary fasteners 62 may then be provided by passing the webs of fastener material through the slip cutter 92 and bonder 94 which intermittently cut the respective webs of fastener material into discrete primary fasteners 62 and bond the primary fasteners 62 to the side margins of the webs of interconnected side panels 86 at spaced apart locations. The slip cutter 92 provides the spacing between the primary fasteners 62 by transferring the individual fasteners away from the slip cutter 92 at a higher speed than the speed at which the webs of fastener material are provided to the slip cutter 92.

Suitable bonding equipment which can be used to provide bonder 94 is well known to those skilled in the art. Desirably, the bonder is an ultrasonic bonder for improved efficiency and cost effectiveness. For example, as illustrated in FIG. 4, the bonder 94 may include the combination of one or more rotary ultrasonic horns 96 and an anvil roll 98 between which the webs to be bonded are passed to provide the bonds. Suitable rotary ultrasonic horns are described in U.S. Pat. No. 5,110,403 to Ehlert, the disclosure of which is hereby incorporated by reference. Such rotary ultrasonic horns 96 generally have a diameter of from about 5 to about 20 centimeters and a width of from about 2 to about 15 centimeters. Alternatively, the ultrasonic horn 96 may be a stationary ultrasonic horn as are also known to those skilled in the art. Other suitable ultrasonic horns and ultrasonic bonders are commercially available from Branson Sonic Power Company, a business having offices in Danbury, Conn. The bonder 94 could otherwise be a thermal or adhesive bonder as are known to those skilled in the art.

The bonder 94 may be configured to provide the desired bonds in a variety of patterns and shapes or sizes. For example, the bonds may be provided as a pattern of points, dots, circles, squares, triangles and the like which may be arranged in a linear or nonlinear configuration. In the illustrated embodiments, such patterns may be located on the bonding horn 96 or the anvil roll 98. Desirably, the pattern is located on the anvil roll 98 for improved manufacturing efficiency.

The webs of interconnected side panels 86 with the primary fasteners 62 intermittently attached thereto may then pass through a cutter 100 and bonder 102 which cut the respective webs of interconnected side panels 86 into discrete panels and intermittently bond the discrete panels to the side edges of the web of interconnected absorbent chassis 80 at spaced apart locations. As illustrated in FIGS. 3 and 4, a portion of each panel is permanently bonded to the side edges of the web of absorbent chassis 80 by bonder 102 to provide the permanent joint 76. In the illustrated embodiments the permanently bonded portions include that portion of the panel which will be located in the back waist region 24 of the diaper 20.

The primary fasteners 62 on the opposite portion of each discrete panel 48 are refastenably engaged with the outer surface 36 of each absorbent chassis 28 on the web 80 to provide the refastenable joint 78 as illustrated in FIG. 3. The refastenable engagement of the primary fasteners 62 with the outer surface 36 of each absorbent chassis 28 on the web of interconnected absorbent chassis 80 may be ensured by passing the primary fasteners 62 and web 80 between a pair of rotating nip rolls (not shown) which apply pressure between the primary fasteners 62 and outer surface 36.

The refastenable portions of the panels may also be releasably bonded to the side edges of the web of absorbent chassis 80 along the refastenable joint 78 as illustrated in FIG. 3. In the illustrated embodiments, the releasable bonds 64 assist the primary fasteners 62 in maintaining the side panels 48 refastenably attached to the absorbent chassis 28 of the diaper 20 in the front waist region 22 of the diaper 20. Such releasable bonds 64 may also be provided by passing the web of interconnected absorbent chassis 80 through bonder 102, as illustrated in FIG. 4. For example, bonder 102 may be configured to releasably bond the portion of the panels longitudinally adjacent the primary fasteners 62 to the side edges 30 of the absorbent chassis 28 of each diaper 20 in the front waist region 22 at releasable bonds 64, as representatively illustrated in FIG. 3.

The term "releasably bond" as used herein refers to a bond which has a relatively low peel strength such that the bond can be broken by the caregiver if desired to assist in inspecting or removing the diaper 20 from the wearer without tearing or severely damaging the other portions of the diaper 20. The releasable bonds may otherwise be broken prior to applying the diaper 20 to the wearer if it is desired to apply the pant-like, refastenable diaper of the present invention in a similar manner to conventional diapers. The specific values of the desired peel strength of the releasable bonds are set forth herein in conjunction with the detailed description of the diaper 20 illustrated in FIGS. 1–3.

The continuous web of interconnected absorbent chassis 80 having the panels attached thereto is then passed through cutter 104 which selectively cuts the web 80 into discrete, individual diapers 20. Such cutters are generally known to those skilled in the art and may include, for example, the combination of a cutting roll 106 and anvil roll 108 through which the web 80 travels. The anvil roll 108 may include a hardened steel rotating roll while the cutting roll 106 may include one or more flexible hardened steel blades clamped on to another rotating roll. The pinching force between the blade on the cutting roll and the anvil roll creates the cut. The cutting roll 106 may have one or more blades depending upon the desired distance between the cuts.

The discrete diapers 20 are then folded in a conventional blade folder 110 about a fold line through the crotch region 26 of the diaper 20. As such, the waist regions 22 and 24 of each diaper are positioned in a facing relationship with the edges of the panels in each waist region extending laterally outward beyond the side edges 30 of the absorbent chassis 28 as illustrated in FIGS. 3 and 4. The fold line extends in a lateral direction through the crotch region 26 of the diaper 20. Desirably, each diaper 20 is consistently folded about fold line such that the waist edges 32 of the diaper 20 in the front and back waist region 22 and 24 align with each other.

Suitable blade folders to provide the folding are well known to those skilled in the art. For example, as illustrated in FIG. 4, the blade folder 110 may include a pair of rotating folding blades 112 which are configured to contact the diaper 20 along the fold line. In such a configuration, the rotation of the folding blades 112 forces the diaper into a nip between two rotating rolls causing the diaper 20 to fold about the fold line.

As illustrated in FIG. 4, the waist regions 22 and 24 are maintained in the facing relationship by passing the diaper 20 through another bonder 114 which may be similar to bonders 94 and 102. The illustrated bonder 114 permanently bonds and secures the front and back panels 70 and 72 of each side panel 48 to each other along side seam 74 as illustrated in FIGS. 1–3 to provide the pant-like diaper 20 of the present invention. Desirably, the bond pattern used along side seam 74 is continuous for improved strength.

Alternatively, if one single piece of material is being used for each side panel 48, the free edges of the side panels 48 may be folded over and bonded by a bonder to the opposite side edge 30 of the absorbent chassis. Desirably, the bonder 114 is also an ultrasonic bonder for improved efficiency and cost effectiveness. Suitable bonders for permanently bonding and securing the panels together or to the absorbent chassis 28 are described above as being suitable for bonder 94. Suitable bond patterns are also described above.

In an alternative method not illustrated, one surface of the primary fasteners 62 may first be refastenably engaged with the side edges of each absorbent chassis on the web of interconnected absorbent chassis 80. The discrete panels cut from the webs of interconnected side panels 86 may then be permanently attached to the opposite surface of the primary fasteners 62 either before or after each diaper is folded depending on whether the side panels 48 are made from a single piece of material or separate pieces such as front and back panels 70 and 72. Such a process may be particularly desirable if the material being used for the individual side panels is a machine direction stretchable material which must be rotated before being applied such as a stretch bonded laminate.

The methods of the present invention, as representatively illustrated in FIG. 4, can reliably and consistently provide refastenable, pant-like disposable absorbent articles having side panels such as those described herein and representatively illustrated in FIGS. 1–3.

PEEL STRENGTH TEST

This test method is designed to quantify, in grams, the peak strength of the releasable bonds assisting the fasteners in refastenably engaging the side panels to the front waist region of the absorbent article. The direction of removal (peel), in this application, is that direction in which the fastener material would generally be removed from a substrate when the product is in use. This direction is generally perpendicular to a longitudinal centerline of the product.

EQUIPMENT

1. Tensile tester capable of obtaining a peak load and equipped with an appropriate load cell. A suitable tensile testing system is a Sintech Tensile Tester, commercially available from MTS Sintech, Research Triangle Park, North Carolina, under the trade designation Instron Model 4201 Tensile Tester with Sintech QAD (Quality Assurance Department) Software.

2. Software commercially obtained from MTS Sintech under the trade designation Sintech Testworks™.

3. Pnuematic-action grips commercially available from Instron Corporation, Canton, Mass., under the trade designation "Instron Model 2712-004."

4. 1 by 4 inch grip faces, serrated, commercially available from Instron Corporation, Canton, Mass.

5. Test facility having a temperature of 23±1° C., and a relative humidity of 50±2 percent.

TEST PROCEDURE

1. A sample to be tested is conditioned in the test facility for at least 4 hours prior to testing.

2. The load cell is calibrated and the software loaded.

3. The grips are installed on the tensile tester with the jaws closed.

4. The test condition for the tensile tester are set as follows:

| | |
|---|---|
| Crosshead speed: | 500 millimeters/minute |
| Full-scale load: | 5 kilograms |
| Threshold: | 5 percent |
| Fail criterion: | 95 percent |
| Gage length: | 50 millimeters |

5. The weight of the clamp is tared out.

6. The primary fastener tab of the fastening element on the side panel of the article is inserted into the upper jaw such that the edge of the grip face is flush with the inner edge of the hook material.

7. The front waist region of the article is inserted into the lower jaw such that the inner surface of the side panel and the outer surface of the front waist region form a 180° angle. The lower jaw is closed.

8. The crosshead is started in motion.

9. The peak load of failure is recorded. It is intended that the mode of failure is that the side panel of the diaper separates from the front waist region of the diaper. Results are rejected if the place of failure is any location other than adjacent the releasable bonds.

SHEAR STRENGTH TEST

This test method is designed to quantify, in grams, the peak dynamic shear strength of the releasable bonds assisting the primary fasteners in refastenably engaging the side panels to the front waist region of the absorbent article. The direction of force in this application is generally perpendicular to the longitudinal centerline of the product.

EQUIPMENT

1. Tensile tester capable of obtaining a peak load and equipped with an appropriate load cell. A suitable tensile testing system is a Sintech Tensile Tester, commercially available from MTS Sintech, Research Triangle Park, N.C., under the trade designation Instron Model 4201 Tensile Tester with Sintech QAD (Quality Assurance Department) Software.

2. Software commercially obtained from MTS Sintech under the trade designation Sintech Testworks™.

3. Pnuematic-action grips commercially available from Instron Corporation, Canton, Mass., under the trade designation "Instron Model 2712-004."

4. 1 by 4 inch grip faces, serrated, commercially available from Instron Corporation, Canton, Mass.

5. Test facility having a temperature of 23±1° C., and a relative humidity of 50±2 percent.

TEST PROCEDURE

1. A sample to be tested is conditioned in the test facility for at least 4 hours prior to testing.

2. The load cell is calibrated and the software loaded.

3. The grips are installed on the tensile tester with the jaws closed.

4. The test condition for the tensile tester are set as follows:

| | |
|---|---|
| Crosshead speed: | 500 millimeters/minute |
| Full-scale load: | 5 kilograms |
| Threshold: | 5 percent |
| Fail criterion: | 95 percent |
| Gage length: | 50 millimeters |

5. The weight of the clamp is tared out.

6. The primary fastener tab of the fastening element on the side panel of the article is inserted into the upper jaw such that the edge of the grip face is flush with the inner edge of the hook material.

7. The front waist region of the article is inserted into the lower jaw such that the inner surface of the side panel and the inner surface of the front waist region are facing the same direction and are parallel to one another. The lower jaw is closed.

8. The crosshead is started in motion.

9. The peak load of failure is recorded. It is intended that the mode of failure is that the side panel of the article separates from the front waist region of the article. Results are rejected if the place of failure is any location other than the releasable bonds.

While the invention has been described in detail with respect to specific aspects thereof, it will be appreciated that those skilled in the art, upon attaining an understanding of the foregoing, may readily conceive of alterations to, variations of and equivalents to these aspects. Accordingly, the scope of the present invention should be assessed as that of the appended claims and any equivalents thereto.

We claim:

1. A method of making a pant-like, refastenable, disposable absorbent article which defines a front waist region, a back waist region, a crotch region which extends between and connects said waist regions, a longitudinal direction and a lateral direction, said method comprising:

a) providing a continuous web of interconnected absorbent chassis wherein each of said absorbent chassis defines an exterior surface, an interior surface opposite said exterior surface, a pair of laterally opposed side edges and a pair of longitudinally opposed waist edges;

b) providing a pair of opposed side panels which define a first side margin and a second side margin opposite said first side margin;

c) permanently attaching said first side margin of said side panels to said side edge of each of said absorbent chassis in one of said front waist region or said back waist region to provide a permanent joint;

d) selectively cutting said continuous web of interconnected absorbent chassis into discrete absorbent articles;

e) folding each of said discrete absorbent articles about a fold line extending in a lateral direction through said crotch region of said article thereby positioning said waist regions in a facing relationship; and f) refastenably attaching said second side margin of said side panels to said side edge of each of said absorbent chassis in said other waist region to provide a refastenable joint thereby providing said pant-like, refastenable, disposable absorbent article.

2. The method of claim 1 wherein said web of interconnected absorbent chassis is provided by:

a) providing a continuous web of outer cover material;

b) positioning a continuous web of bodyside liner material in a superposed relation to said outer cover material; and c) intermittently placing individual absorbent cores between said outer cover material and said bodyside liner material at spaced apart locations.

3. The method of claim 1 wherein said permanently attaching includes ultrasonically bonding said first side margins of said side panels to said side edges of said absorbent chassis in said one waist region to provide said permanent joints.

4. The method of claim 1 wherein said refastenably attaching includes refastenably engaging a fastener located on each of said second side margins of said side panels to said exterior surface of each of said absorbent chassis in said other waist region to provide said refastenable joint.

5. The method of claim 4 wherein said fasteners are hook and loop type fasteners.

6. The method of claim 5 wherein said fasteners are refastenably engaged directly to an outer cover material of said absorbent chassis.

7. The method of claim 4 wherein said refastenably attaching includes ultrasonically bonding said second side margins of said side panels to said side edges of said absorbent chassis in said other waist region to assist said fasteners in providing said refastenable joints.

8. The method of claim 7 wherein said second side margins of said side panels are ultrasonically bonded to said side edges of said absorbent chassis with releasable point bonds located longitudinally adjacent both longitudinal ends of said fasteners.

9. The method of claim 7 wherein said second side margins of said side panels are releasably bonded to said side edges of said absorbent chassis to define a peel strength of no more than about 1500 grams.

10. The method of claim 1 wherein said refastenably attaching includes:
a) refastenably engaging a fastener to said exterior surface of each of said absorbent chassis adjacent each of said side edges of said absorbent chassis; and
b) overlaying and permanently bonding said second side margins of said side panels to said fasteners to provide said refastenable joints.

11. The method of claim 10 wherein said fasteners are hook and loop type fasteners.

12. A method of making a pant-like, refastenable, disposable absorbent article which defines a front waist region, a back waist region, a crotch region which extends between and connects said waist regions, a longitudinal direction and a lateral direction, said method comprising:
a) providing a continuous web of interconnected absorbent chassis wherein each of said absorbent chassis defines an exterior surface, an interior surface opposite said exterior surface, a pair of laterally opposed side edges and a pair of longitudinally opposed waist edges;
b) permanently attaching a pair of laterally opposed back panels to said side edges of each of said absorbent chassis in one of said front waist region or said back waist region of said absorbent article to provide a permanent joint;
c) refastenably attaching a pair of laterally opposed front panels to said side edges of each of said absorbent chassis in said opposite waist region of said absorbent article to provide a refastenable joint;
d) selectively cutting said continuous web of interconnected absorbent chassis into discrete absorbent articles;
e) folding each of said discrete absorbent articles about a fold line extending in a lateral direction through said crotch region of said article thereby positioning said front panels and said back panels in a facing relationship; and
f) connecting said front panels and said back panels together along a pair of laterally opposed side seams to define a waist opening and a pair of leg openings and provide said pant-like, refastenable, disposable absorbent article.

13. The method of claim 12 wherein said permanently attaching includes ultrasonically bonding side margins of said back panels to said side edges of said absorbent chassis in said one waist region to provide said permanent joints.

14. The method of claim 12 wherein said refastenably attaching includes refastenably engaging a fastener located on side margins of said front panels to said exterior surface of each of said absorbent chassis in said other waist region to provide said refastenable joint.

15. The method of claim 14 wherein said fasteners are hook and loop type fasteners.

16. The method of claim 15 wherein said fasteners are refastenably engaged directly to an outer cover material of said absorbent chassis.

17. The method of claim 14 wherein said refastenably attaching includes ultrasonically bonding said side margins of said front panels to said side edges of said absorbent chassis in said other waist region to assist said fasteners in providing said refastenable joints.

18. The method of claim 17 wherein said side margins of said front panels are releasably bonded to said side edges of said absorbent chassis to define a peel strength of no more than about 1500 grams.

19. The method of claim 12 wherein said refastenably attaching includes:
a) refastenably engaging a fastener to said exterior surface of each of said absorbent chassis adjacent each of said side edges of said absorbent chassis; and
b) overlaying and permanently bonding side margins of said front panels to said fasteners to provide said refastenable joints.

20. The method of claim 19 wherein said fasteners are hook and loop type fasteners.

21. A method of making a pant-like, refastenable, disposable absorbent article which defines a front waist region, a back waist region, a crotch region which extends between and connects said waist regions, a longitudinal direction and a lateral direction, said method comprising:
a) providing a continuous web of interconnected absorbent chassis wherein each of said absorbent chassis defines an exterior surface, an interior surface opposite said exterior surface, a pair of laterally opposed side edges and a pair of longitudinally opposed waist edges;
b) intermittently providing a pair of laterally opposed side panels which define a front portion and a back portion;
c) permanently attaching said back portions of said opposed side panels to said side edges of each of said absorbent chassis in one of said front waist region or said back waist region of said absorbent article to provide a permanent joint;
d) refastenably attaching said front portions of said opposed side panels to said side edges of each of said absorbent chassis to provide a refastenable joint;
e) selectively cutting said continuous web of interconnected absorbent chassis into discrete absorbent articles along a cutting line which intersects said side panels between said front portion and said back portion;
f) folding each of said discrete absorbent articles about a fold line extending in a lateral direction through said crotch region of said article thereby positioning said front portions and said back portions of said side panels in a facing relationship; and g) connecting said front portions and said back portions together along a pair of laterally opposed side seams to define a waist opening and a pair of leg openings and provide said pant-like, refastenable, disposable absorbent.

22. The method of claim 21 wherein said permanently attaching includes ultrasonically bonding side margins of said back portions to said side edges of said absorbent chassis in said one waist region to provide said permanent joints.

23. The method of claim 21 wherein said refastenably attaching includes refastenably engaging a fastener located on side margins of said front portions to said exterior surface of each of said absorbent chassis in said other waist region to provide said refastenable joint.

24. The method of claim 23 wherein said fasteners are hook and loop type fasteners.

25. The method of claim 24 wherein said fasteners are refastenably engaged directly to an outer cover material of said absorbent chassis.

26. The method of claim 23 wherein said refastenably attaching includes ultrasonically bonding said side margins of said front portions to said side edges of said absorbent chassis in said other waist region to assist said fasteners in providing said refastenable joints.

27. The method of claim 26 wherein said side margins of said front portions are releasably bonded to said side edges of said absorbent chassis to define a peel strength of no more than about 1500 grams.

* * * * *

(12) EX PARTE REEXAMINATION CERTIFICATE (7803rd)
United States Patent
Vogt et al.

(10) Number: US 6,113,717 C1
(45) Certificate Issued: Oct. 12, 2010

(54) METHOD OF MAKING REFASTENABLE, PANT-LIKE DISPOSABLE ABSORBENT ARTICLES

(75) Inventors: Robert Eugene Vogt, Neenah, WI (US); Timothy James Blenke, Neenah, WI (US)

(73) Assignee: Kimberly-Clark Worldwide, Inc., Neenah, WI (US)

Reexamination Request:
No. 90/010,843, Feb. 1, 2010

Reexamination Certificate for:
Patent No.: 6,113,717
Issued: Sep. 5, 2000
Appl. No.: 09/215,491
Filed: Dec. 18, 1998

(51) Int. Cl.
*A61F 13/49* (2006.01)
*A61F 5/44* (2006.01)
*A61F 13/15* (2006.01)
*A61F 13/496* (2006.01)

(52) U.S. Cl. .................... 156/73.1; 156/227; 156/264; 156/269

(58) Field of Classification Search .................. 156/73.1
See application file for complete search history.

(56) References Cited

U.S. PATENT DOCUMENTS 5,496,298 A    3/1996   Kuepper et al.

FOREIGN PATENT DOCUMENTS

| JP | 3-195555 A | 8/1991 |
| JP | 7-80023 A | 3/1995 |

*Primary Examiner*—Alan Diamond

(57) ABSTRACT

A method of making a refastenable, pant-like, disposable absorbent article includes attaching a pair of opposed side panels to the side edges of an absorbent chassis such hat they extend laterally outward from and between the front and back waist regions of the article. One of the side margins of each side panel is permanently attached to the side edge of the absorbent chassis in one of the waist regions and the other side margin of each side panel is refastenably attached to the side edge of the absorbent chassis in the opposite waist region. The side panels are refastenably attached before the articles is packaged to provide the pant-like disposable absorbent article.

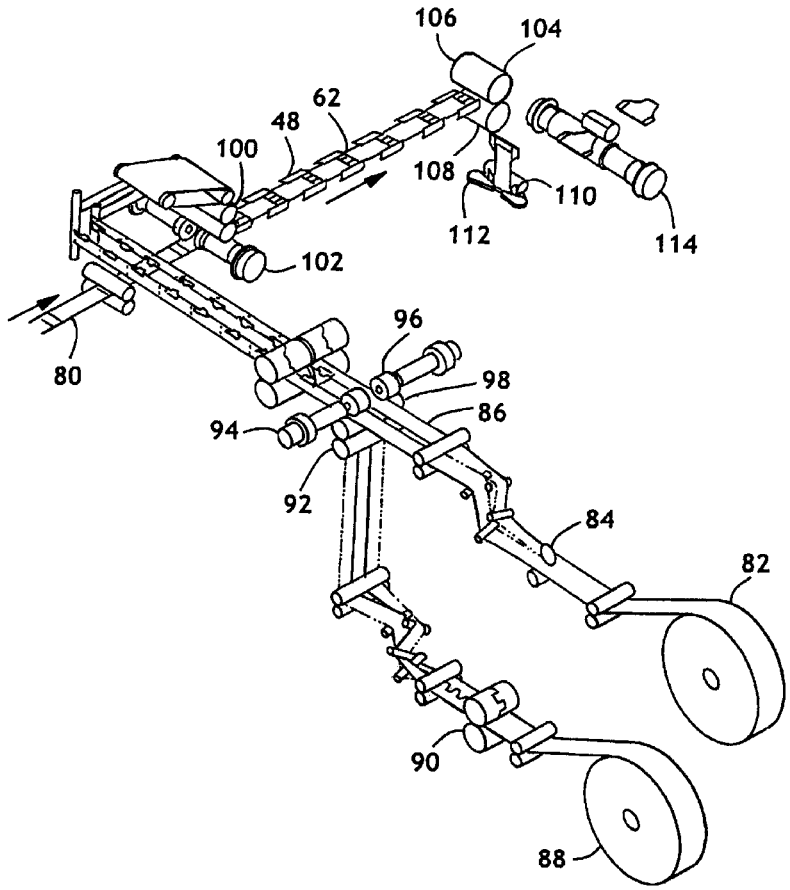

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-27 is confirmed.

* * * * *